(12) United States Patent
Swanson

(10) Patent No.: US 9,723,381 B2
(45) Date of Patent: Aug. 1, 2017

(54) ATHLETIC MONITORING SYSTEM HAVING AUTOMATIC PAUSING OF MEDIA CONTENT

(71) Applicant: NIKE, Inc., Beaverton, OR (US)

(72) Inventor: Evan Swanson, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 336 days.

(21) Appl. No.: 14/309,574

(22) Filed: Jun. 19, 2014

(65) Prior Publication Data

US 2015/0181314 A1 Jun. 25, 2015

Related U.S. Application Data

(60) Provisional application No. 61/920,286, filed on Dec. 23, 2013.

(51) Int. Cl.

| G08C 19/22 | (2006.01) |
|---|---|
| H04Q 9/00 | (2006.01) |
| G08C 15/06 | (2006.01) |
| G08B 23/00 | (2006.01) |
| G08B 21/00 | (2006.01) |
| G08B 1/00 | (2006.01) |
| H04Q 1/30 | (2006.01) |
| G08B 1/08 | (2006.01) |
| G01C 21/20 | (2006.01) |
| G06F 19/00 | (2011.01) |
| G01S 19/49 | (2010.01) |
| G01S 5/02 | (2010.01) |
| A63B 24/00 | (2006.01) |
| G01S 19/19 | (2010.01) |

(52) U.S. Cl.
CPC .......... *H04Q 9/00* (2013.01); *A63B 24/0062* (2013.01); *G01C 21/20* (2013.01); *G01S 5/0263* (2013.01); *G01S 19/19* (2013.01); *G01S 19/49* (2013.01); *G06F 19/3481* (2013.01)

(58) Field of Classification Search
CPC .... G06F 19/3481; G01S 19/49; G01S 5/0263; G01C 21/20
See application file for complete search history.

(56) References Cited

U.S. PATENT DOCUMENTS

| 2009/0138507 A1 | 5/2009 | Burckart et al. |
| 2010/0056341 A1 | 3/2010 | Ellis et al. |

(Continued)

FOREIGN PATENT DOCUMENTS

| JP | 2007020977 A | 2/2007 |
| JP | 2009259102 A | 11/2009 |
| JP | 2013138880 A | 7/2013 |

OTHER PUBLICATIONS

Jan. 15, 2015—ISR and WO—App. No. PCT/US2014/045732.

*Primary Examiner* — Firmin Backer
*Assistant Examiner* — Jerold Murphy
(74) *Attorney, Agent, or Firm* — Banner & Witcoff, Ltd.

(57) ABSTRACT

Systems and methods configured to be worn on a body of user for athletic performance monitoring, and having a sensor for capturing data associated with an athletic activity being carried out by the user. The captured sensor data may be used to identify a break in an athletic training session being carried out by the user, and in response, to automatically pause playback of media content to the user.

7 Claims, 27 Drawing Sheets

(56) References Cited

U.S. PATENT DOCUMENTS

| | | | |
|---|---|---|---|
| 2010/0178873 A1* | 7/2010 | Lee | H04M 1/7253 455/41.3 |
| 2012/0062357 A1 | 3/2012 | Slamka | |
| 2012/0274508 A1* | 11/2012 | Brown | G04F 10/00 342/357.25 |
| 2013/0268101 A1 | 10/2013 | Brammer | |

* cited by examiner

ATHLETIC MONITORING SYSTEM HAVING AUTOMATIC PAUSING OF MEDIA CONTENT

CROSS REFERENCE TO RELATED APPLICATIONS

This application claims the benefit of U.S. Provisional Application Ser. No. 61/920,286, entitled "Athletic Monitoring System having Automatic Pausing of Media Content," filed Dec. 23, 2013, which application is incorporated by reference in its entirety for any and all non-limiting purposes.

FIELD

This invention relates generally to athletic performance sensing, monitoring, and/or tracking systems and methods. Such systems may include components for sensing athletic performance data and/or for storing and displaying desired information (e.g., athletic performance information) to the user. Systems in accordance with at least some aspects of this invention facilitate transfer of athletic performance data from the performance sensing system to a processing system and/or a display device, e.g., to enable data input, storage, analysis, and/or display on or by an electronic display device, including on or by conventional electronic display devices that are known and commercially available (e.g., including devices that are not typically designed and adapted for displaying athletic performance data, such as portable music and/or other audio/video display or playback devices). Systems and methods according to at least some examples of this invention allow much user control of and/or variation in entertainment, motivational, and other audio/video content presented to the user via an electronic device during an athletic performance.

BACKGROUND

Modern technology has given rise to a wide variety of different electronic and/or communication devices that keep users in touch with one another, entertained, and informed. A wide variety of portable electronic devices are available for these purposes, such as: cellular telephones; personal digital assistants ("PDAs"); pagers; beepers; MP3 or other audio playback devices; radios; portable televisions, DVD players, or other video playing devices; watches; GPS systems; etc. Many people like to carry one or more of these types of devices with them when they exercise and/or participate in athletic events, for example, to keep them in contact with others (e.g., in case of inclement weather, injuries; or emergencies; to contact coaches or trainers; etc.), to keep them entertained, to provide information (e.g., time, direction, location, etc.), and the like.

Athletic performance monitoring systems also have benefited from recent advancements in electronic device and digital technology. Electronic performance monitoring devices enable easy and convenient monitoring of many physical or physiological characteristics associated with exercise or other athletic performances, including, for example: speed and distance data, altitude data, GPS data, heart rate, pulse rate, blood pressure data, body temperature, etc. Such systems, however, have deficiencies, for example, in their portability, convenience, customizability, and/or user friendliness.

SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to a more detailed description provided below.

Aspects of the systems and methods described herein relate to athletic performance monitoring systems configured to be worn on a body of a user, and having a sensor for capturing data associated with an athletic activity being carried out by the user. Accordingly, the captured sensor data may be used to identify a break in an athletic training session being carried out by the user, and in response, to automatically pause playback of media content to the user.

In another aspect, this disclosure relates to an apparatus having a processor, a location-sensing sensor, e.g., GPS, configured to obtain location information, and a media content interface for playing music to a user. This apparatus may be configured to determine geographic location of the user. In yet other embodiments, the device may receive a determined geographic location. This information may be from, or derived, from GPS, radar, Doppler, triangulation, and/or one or more other methods. The geographic location of the user with may be combined with a planned route for the user. Furthermore, this apparatus may be configured to identify a intersection (which may of two or more different paths, including a road, railroad, bike path, sidewalk, running path, and/or combinations thereof) in proximity to the user. In one embodiment, an intersection may be detected up ahead of the user (e.g., in the general direction of the user's travel and/or in accordance with a planned or estimated route). In response, certain embodiments may pause (or stop) playback of media content until the user has traveled through the road intersection. In certain embodiments, it may be determined that the user is at least a first distance past the intersection.

In yet another aspect, this disclosure relates to a unitary apparatus configured to be worn by a user, and having a processor, a sensor, and a media content interface. The apparatus is configured to receive or capture motion information from the sensor, and using the motion information, identify an athletic training session. The apparatus is further configured to identify a stoppage/break in the identified athletic training session, and in response, pause playback of media content to a user.

In another aspect of this disclosure relates to an apparatus having a processor, sensor, and a memory. The apparatus is configured to capture data from the sensor and compare the captured data to the threshold. Accordingly, if a value of the data exceeds the threshold value, the apparatus is configured to pause playback of media content to a user.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
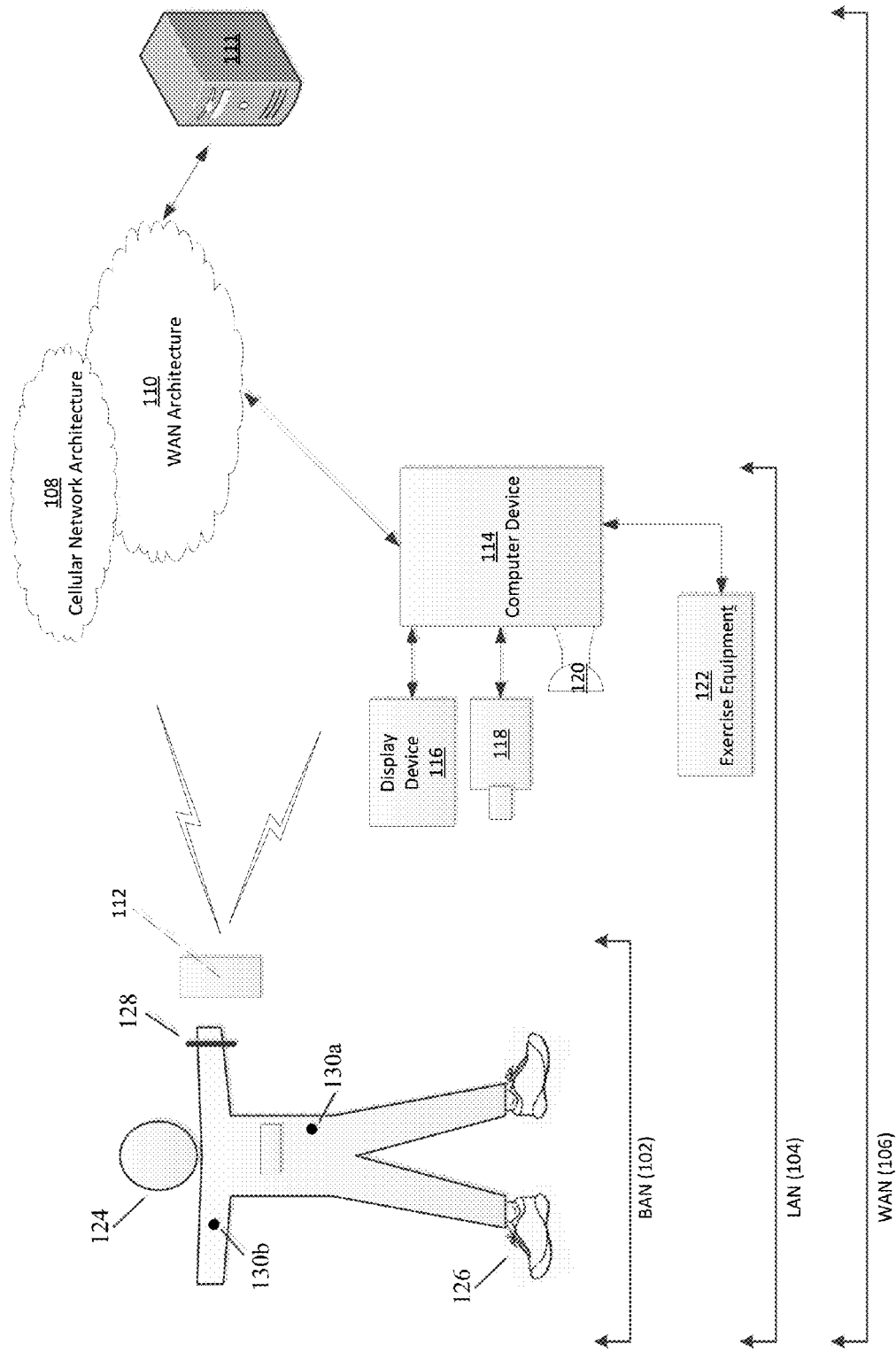
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Those skilled in the art will appreciate that the design and structure of computer device 114 may vary depending on several factors, such as its intended purpose. One example implementation of computer device 114 is provided in FIG.

Figure 2:
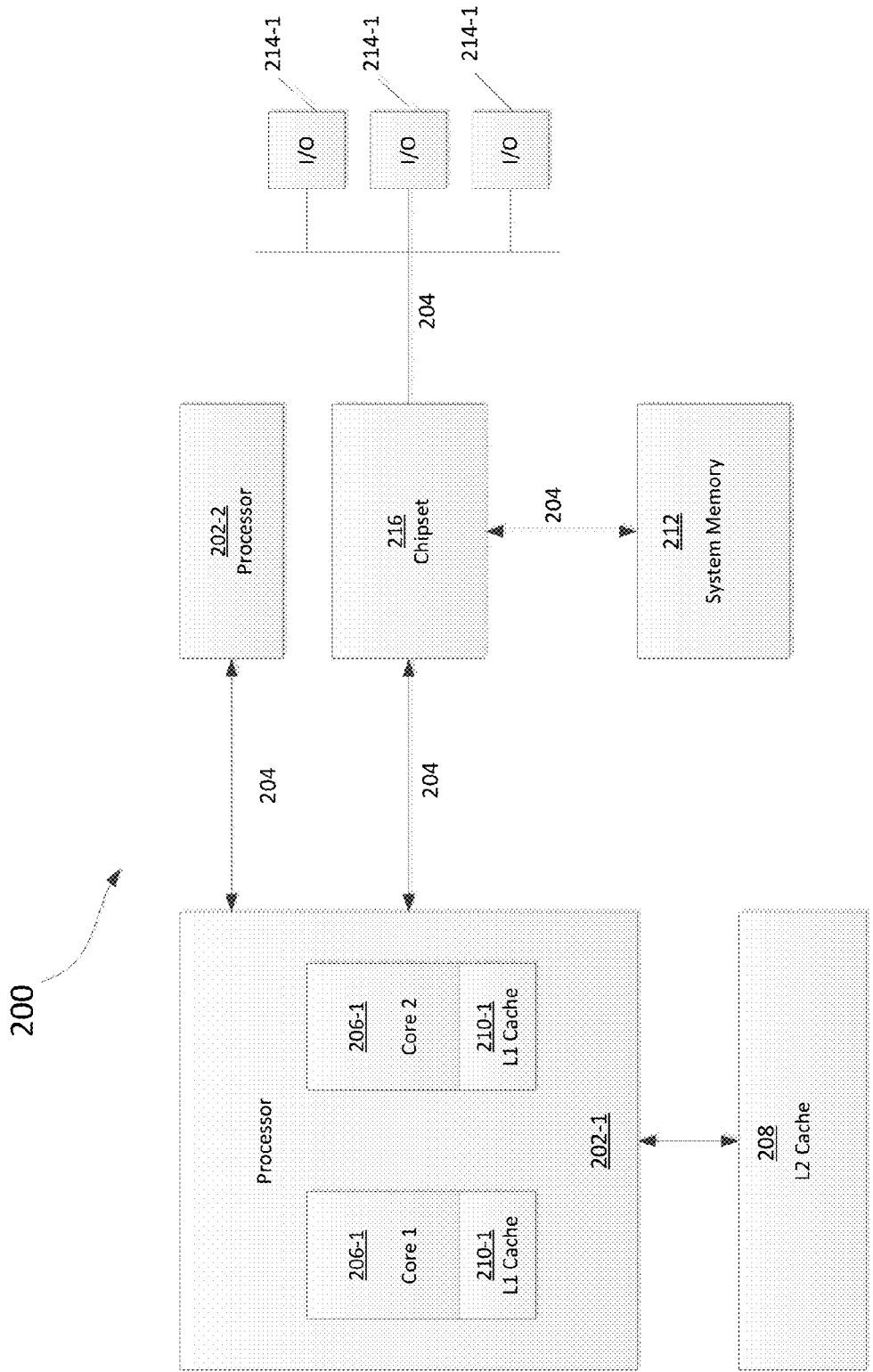
FIG. 2 illustrates an example computer device that may be part of or in communication with the system of FIG. 1.

2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 118 and/or sensor 128 may comprise one or more thermal imaging devices. In one embodiment, image-capturing device 118 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
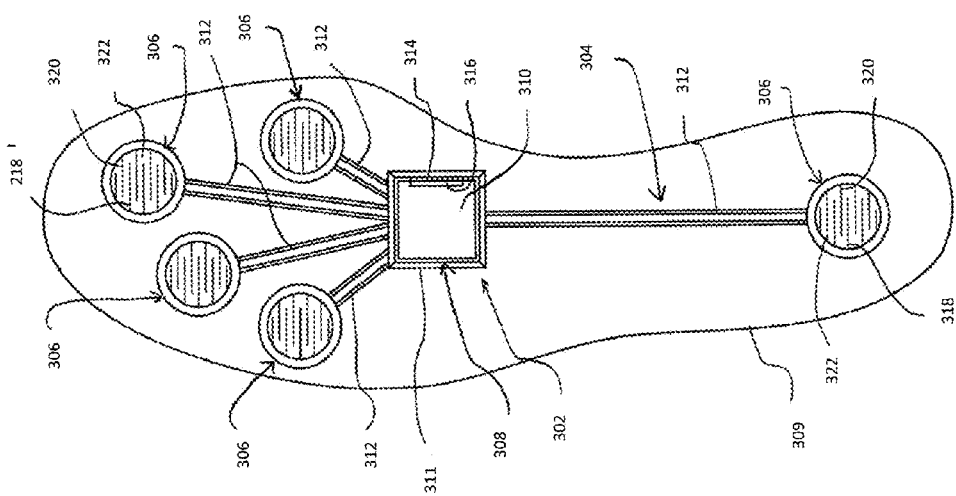
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310.

The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
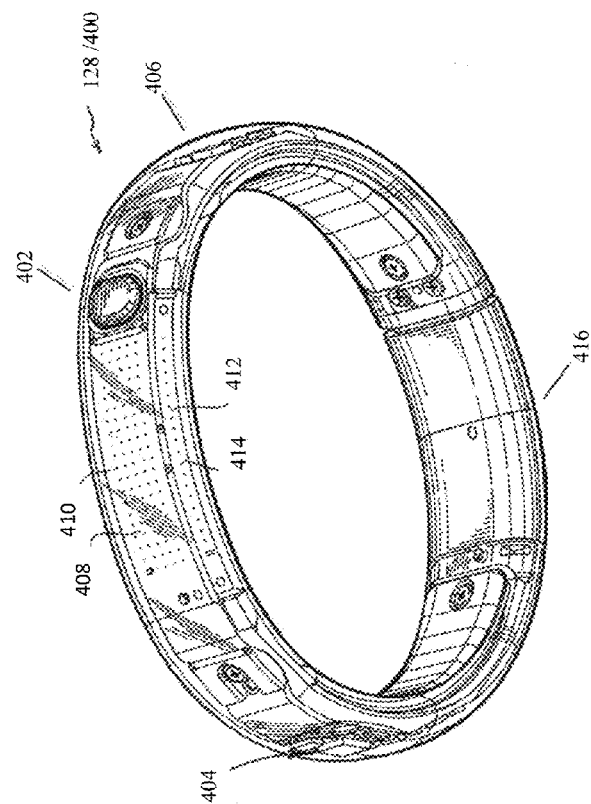
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
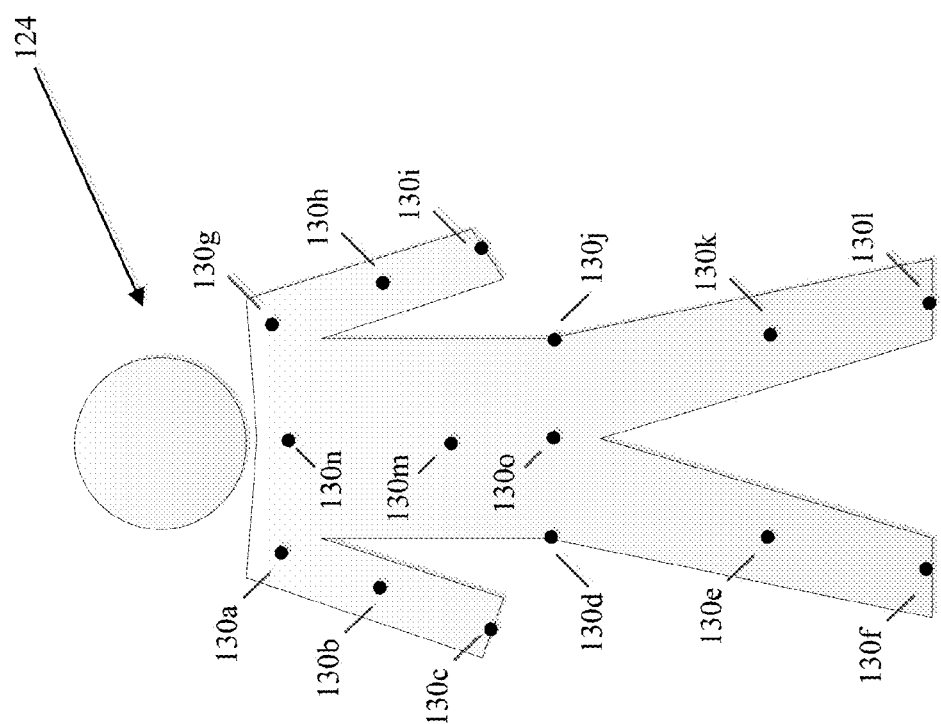
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130*m* may be utilized in a determination of the user's center of gravity (a.k.a, center of mass). For example, relationships between location 130*a* and location(s) 130*f*/130*l* with respect to one or more of location(s) 130*m*-130*o* may be utilized to determine if a user's center of gravity has been elevated along the vertical axis (such as during a jump) or if a user is attempting to "fake" a jump by bending and flexing their knees. In one embodiment, sensor location 130*6n* may be located at about the sternum of user 124. Likewise, sensor location 130*o* may be located approximate to the naval of user 124. In certain embodiments, data from sensor locations 130*m*-130*o* may be utilized (alone or in combination with other data) to determine the center of gravity for user 124. In further embodiments, relationships between multiple sensor locations, such as sensors 130*m*-130*o*, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130*m*-130*o* may serve as a point for a center of moment location of user 124. In another embodiment, one or more locations may serve as a center of moment of specific body parts or regions.

Figure 6:
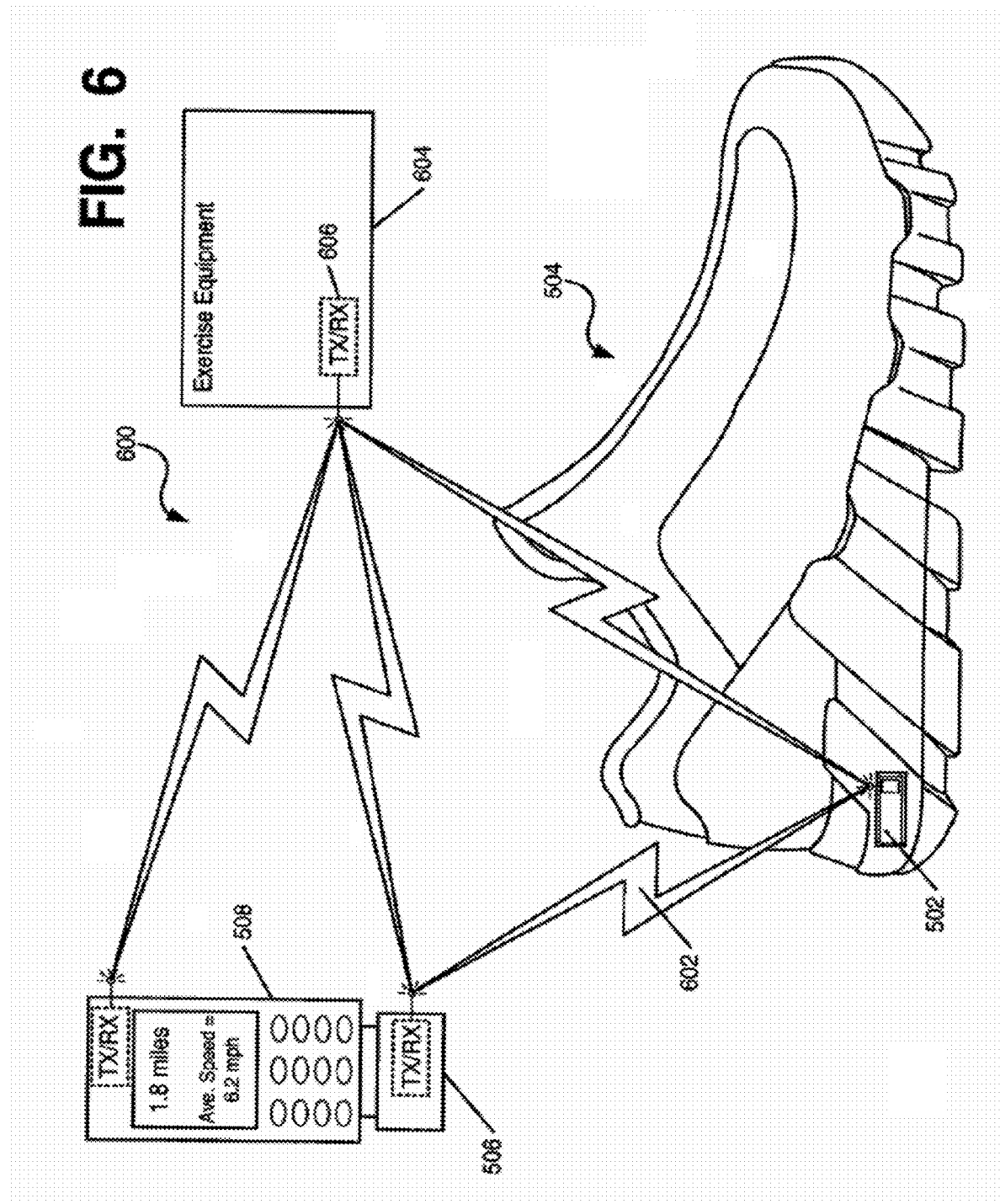
FIG. 6 illustrates an example of electronic communications between athletic performance sensing systems in accordance with at least some examples of this invention and external equipment.
Figure 7:
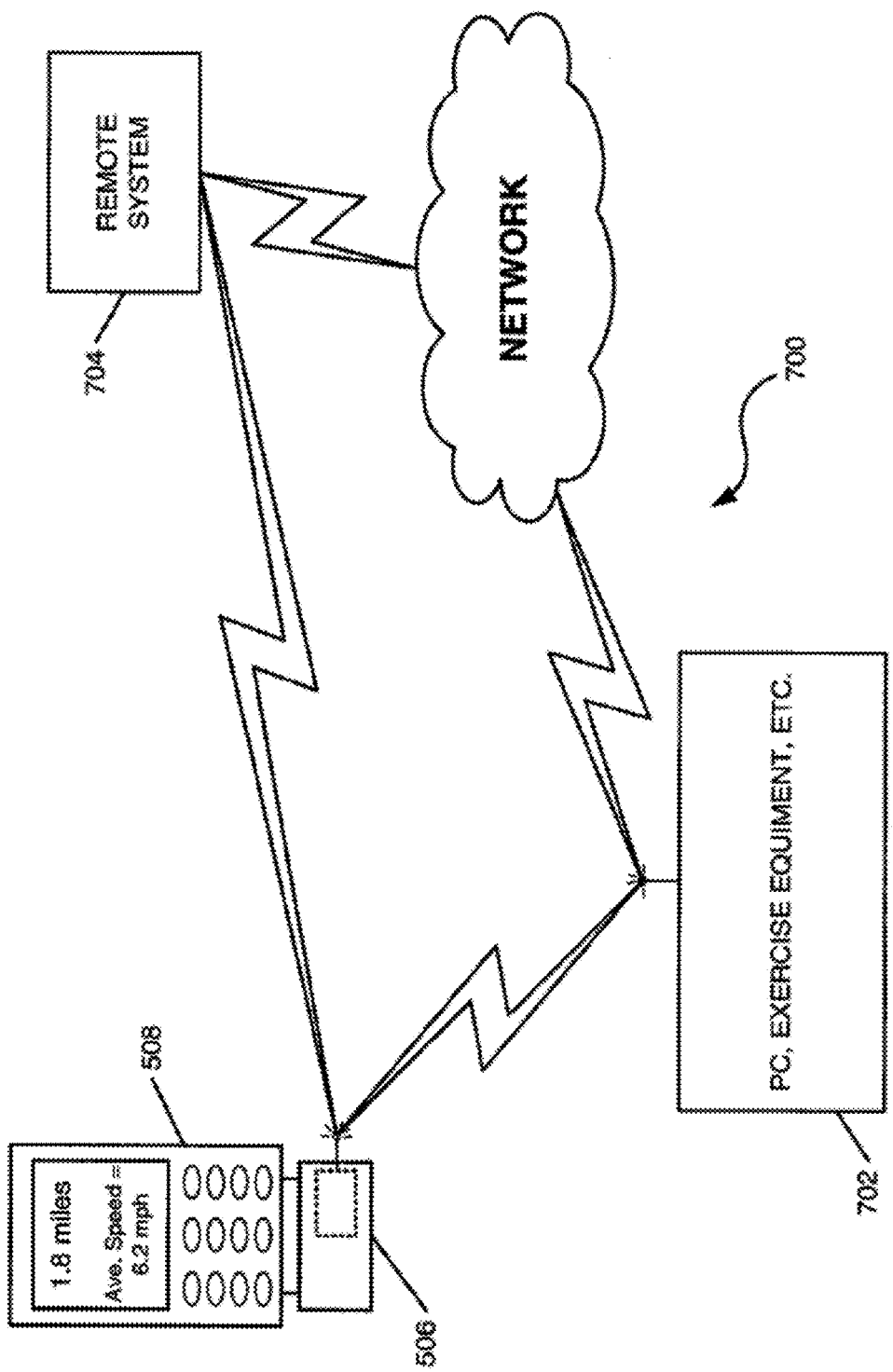
FIG. 7 illustrates an example of electronic communications between athletic performance sensing systems in accordance with at least some examples of this invention and remote systems, e.g., systems for storing, tracking, and/or analyzing the performance data and/or systems for providing workout routines and/or other data.

II. Description of Example Athletic Performance Sensing and Tracking Systems According to this Invention FIGS. 6 and 7 illustrate additional features of and environments of use for example performance sensing and tracking systems and methods in accordance with this invention. In addition to running or walking on an open course using pedometer based speed and distance information (or other sensed information), systems and methods in accordance with at least some examples of this invention may be useful to sense and/or track athletic performance characteristics at other locales, such as in a gym or spa, in workout classes, at home, and the like. The system 600 of FIG. 6 illustrates the performance module 502 (e.g., carried by the athlete during the performance, such as in an article of footwear 504, as part of the athlete's clothing, an article worn by the athlete, etc.) in communication with a portable electronic device 508 via an interface device 506. See transmission indicator 602 in FIG. 6. In addition to this communication, as illustrated in FIG. 6, any or all of the module 502, interface device 506, and/or electronic device 508 may be configured to exchange data with one or more pieces of exercise equipment 604 or other things, e.g., equipment or transceiver devices included in a gym, spa, or other athletic performance setting.

Reference number 604 in FIG. 6 may indicate any type of exercise equipment and/or gym, spa, home, or other athletic performance setting. For example, reference number 604 may represent a wide variety of different types of athletic and/or training equipment, including, for example: training machines commonly found in a gym, such as treadmills, spinning machines, elliptical training machines, stationary bicycles, stair climbing machines, cross-country ski simulating machines, weight lifting machines, rowing machines, etc. Additionally or alternatively, reference number 604 may represent various performance locales that may or may not directly involve the use of training machines, such as facilities (e.g., training rooms) used for yoga, dance, pilates, martial arts training, stretching, weight lifting, tae bo, boxing, wrestling, etc. As yet another example or alternative, reference number 604 may represent or include an input device through which a user can enter information regarding the athletic or training activities he/she has done or plans to do, such as track and/or field training or events, team sporting events, free weight lifting, etc. Reference number 604 also may relate to a physical or physiological parameter measuring system, such as a scale, heart rate monitor, blood pressure measuring system, body temperature measuring system, etc. Using systems like those illustrated in FIG. 6, users can use element 604 to produce input for tracking any desired type of athletic or training activity with which they are involved and/or physical or physiological parameter relating to their training.

A wide variety of different types of data and information may be exchanged between the exercise equipment 604 (or other workout or athletic performance setting or equipment) and the portable equipment kept by the user (e.g., module 502, interface device 506, and/or electronic device 508). For example, if desired, the equipment 604 may be designed to send information to the user's equipment (e.g., via transmission/reception system 606) relating to the workout parameters of an individual workout or training exercise, such as: data detectable or sensed by gym or workout equipment, such as distance traveled, speed, elevation changes, number of steps, number of floors climbed, overall time, speed or other data as a function of time, calories burned, revolutions per minute, number of rotations, resistance settings, hill or incline information, amount of weight lifted, number of repetitions, weight machines used, etc. Any measured physiological characteristics also may be sent to the user's portable equipment, such as heart rate, pulse rate, blood pressure, blood oxygen levels, EEG data, EKG data, body temperature, air intake/expel rates, etc. Transmission/reception system 606 also may send identification information, such as an exercise machine identification, room identification, location information, other equipment identification information, etc. The desired data may be sent to the user's portable equipment at any desired time, such as in real time (as it is being collected at the equipment 604), periodically, after the exercise is complete, as the user leaves the gym facility, etc.

For systems using pedometer based information, in addition to detecting speed and/or distance information, it is useful in at least some example systems and methods according to this invention for the sensing system to measure or detect data and information relating to the user's cadence, rhythm, or "beat" associated with the athletic performance activity (e.g., steps, rotations, foot movement direction changes, arm movement direction changes, etc., with respect to time, such as steps per second, revolutions per minute, stair-stepper steps per second, rowing strokes per minute, etc.). An accelerometer and/or direction change sensor may be used in determining cadence. The module 502 and/or other portions of the portable equipment (e.g., interface device 506 and/or electronic device 508) and/or the equipment 604 may be used to provide data and information relating to user cadence. Cadence information may be collected with respect to a wide variety of athletic performance activities, including many activities that take place in a gym using exercise equipment, such as running or walking on a treadmill, spinning, elliptical training, stationary bicycle training, stair-stepper training, cross-country skiing simulation, rowing simulation, etc. In addition to providing data relating to the athletic performance, cadence information also may be useful in systems and methods according to at least some examples of this invention for selection of motivational, inspirational, performance enhancing, or other media content during the athletic performance (e.g., for song selection and the like), as will be described in more detail below.

When reference number 604 represents a facility or locale, it may simply send information identifying the location and/or timing information (such as time spent at the location). For example, reference number 604 may include an RFID or other data transmission device 606 that communicates with the user's portable equipment to indicate when a user enters or leaves a certain room or area (such as a weight lifting room; an aerobics, yoga, or pilates studio; a martial arts training facility; etc.) and/or to indicate the amount of time the user spent at that location (such as actual entry and/or exit times, date information, overall time spent, etc.). If a specific locale may be used for numerous activities, scheduling or other information also may be provided and/or transmitted so that the transmission device 606 also may be capable of automatically transmitting the type of activity with which the user was involved when present at the location or facility. Such data can help users create and/or maintain a detailed tracking and/or complete log of their workout activities, e.g., even in situations where no physical or physiological data can be provided by the sensors. Optionally, if desired, users can include additional information in their workout calendar or log, e.g., for tracking purposes, such as user location data; flight or hotel stay information; menstrual cycle data; athletic event calendar information; target or goal date information; and any desired historical, future, calendar, or goal information.

Data also may be transferred from the user's portable equipment (e.g., module 502, interface device 506, and/or electronic device 508) to the exercise equipment or other workout or athletic performance setting 604. For example, user ID information may be transmitted so that the exercise equipment or other workout or athletic performance setting 604 can store workout data associated with the specific user. As another example, if desired, the user's portable equipment (e.g., module 502, interface device 506, and/or electronic device 508) may be used, at least in part, to control the exercise equipment or other workout or athletic performance setting 604, e.g., to make the workout machine settings correspond to a workout pre-programmed into or downloaded to the user's portable equipment. For example, workout information downloaded from a workout routine stored in or available through the portable equipment may be used to control various features of the workout, such as: weight machine settings, resistance settings, incline (or hill level) settings, target distance (or other overall time length or duration) settings, target calorie burn (or other physiological based parameter) settings, treadmill speed or incline settings, etc. As yet another example, if desired, the user's portable equipment may send workout identification information (e.g., Workout 12) to the exercise equipment or other workout or athletic performance setting 604, which then may use this identification information to provide the desired settings for the identified workout from information stored in memory. Data collected as a workout progresses (e.g., via module 502, etc.) also may be used, if desired, to control the exercise equipment or other workout or athletic performance devices (e.g., to set or change intensity or resistance levels, to shorten or lengthen workout times, etc.). Of course, other information also may be transmitted from the user's portable equipment to element 604.

As another potential option or alternative, if desired, the user's portable equipment (e.g., module 502, interface device 506, and/or electronic device 508) may be programmed and adapted to send information to the exercise equipment 604, e.g., for display by the exercise equipment 604, for transmission to a remote source (e.g., via a network maintained at the gym or spa, etc.), etc. As more specific examples, as described in more detail below, the electronic device 508 may be a playback device that presents audio and/or video information to the user, such as music, videos, and/or other entertainment content. If desired, systems and methods according to at least some examples of this invention may be arranged and adapted to send this content from or through the electronic device 508 (or other user carried portable equipment) to the exercise equipment 604 (or another device), so that the media (or other) content may be displayed or presented on a screen or other output device provided with the exercise equipment 604 (e.g., an input panel, a touch panel, a television screen, an audio output system, etc.). Furthermore, if desired, in such systems, the input panel or other portion of the exercise equipment 604 may be programmed and adapted to receive user input controlling the playback features of the media content (e.g., to skip songs or other content, replay songs or other content, select songs or other content for presentation, etc.).

FIG. 7 illustrates additional features that may be present in example athletic performance sensing and/or tracking systems and methods according to this invention. The arrangement 700 shown in FIG. 7 allows users to send data and information to and/or receive data and information from one or more remote sources, such as from one of the portable devices (e.g., module 502, interface device 506, and/or electronic device 508) to a personal computer (e.g., at the user's home or office) or other computer station 702 (which may include the workout equipment itself and/or a computer maintained at the gym or other facility) and/or to a remote system 704 (optionally via a network connection, such as over the Internet), which may be maintained and operated by the user, by a fitness center, by a gym, or by another third party. This arrangement 700 may allow for more convenient storage, maintenance, retrieval, and further processing of the collected athletic performance data (e.g., as compared to limiting the user interface, data processing, and/or computational capabilities of the overall system to operations performed through the electronic device 508 and/or interface 506).

In addition to storing historical data and information, this arrangement 700 allows downloading of data and information from one or more remote systems 704 to the user, e.g., to the PC or other equipment 702 and/or to the portable device 508 (optionally through the interface device 506). Data also may originate in the PC or other equipment 702 (without the use of a remote computer 704) and be sent to the user's portable equipment 506 and/or 508. In some instances, the remote system 704 (or system 702) may be accessed by multiple users (e.g., over a network, such as the internet or a gym based network), and such systems may provide a wide variety of data and information to users (e.g., each individual user may have his/her own webpage(s), user ID, password, etc.). While potential content of this exchanged data and information will be described in more detail below in conjunction with FIGS. 8 through 19, as examples, this downloaded data and information may include: pre-programmed workouts; music or other audio/video content; pre-programmed workouts mixed with music or other audio/video content including coaching and/or motivational content; comparative data; coaching, safety, and/or motivational content; and the like.

III. Description of Example Features of Systems and Methods According to this Invention One feature of systems and methods according to at least some examples of this invention relates to the ability to sense and track information relating to a wide variety of types of athletic performance activities. Data relating to athletic performances can be entered into systems and methods according to the invention automatically, semi-automatically, and/or manually. More specific examples follow.

When performing athletic activities using exercise machines (e.g., like those present in a gym, spa, home, etc.), users can get immediate feedback, data, and information relating to their activities on their portable electronic device 508, including data and information produced by the module 502 and/or data and information collected or measured by the exercise or other equipment 604. This may be accomplished, for example, using a system 600 like that shown in FIG. 6. If desired, the equipment 604 may transmit (automatically, in response to user input, in response to activation of an RFID transmission system, etc.) some type of identifying data or information so that the electronic device 508 or other portion of the user carried portable equipment can store information to track one or more of: the type of workout activity (e.g., type of machine, etc.), the length of the workout, one or more parameters associated with the workout, etc.

Some athletic performance activities do not utilize machines, but they may be performed in a specially designated room or area of a building or facility. As described above, a transmission device (e.g., device 606) may be provided at the locale to automatically, semi-automatically, or manually transmit data indicating the location or room at which the user was present, optionally along with the type of activity that took place while there (e.g., based on schedule or other information, for example, to indicate that the user participated in a dance class, pilates class, aerobics class, martial arts training, lifted weights, etc.). The room may include a wireless transmission system (optionally activated by an individual user, e.g., by pressing a button, turning on a light, signing in, signing out, opening the door, etc.) that sends data indicating, for example, the room identification, the type of activity to be conducted at that time in the room (e.g., karate class, etc.), user entry time, user exit time, etc. This transmitted data may be received, for example, by the module 502, interface 506, and/or electronic device 508 and stored. In some instances, the sensor included with the module 502 (if any) may be able to detect at least some data associated with these types of workouts, even if no machine is directly involved, such as information relating to step count, heart rate, pulse rate, cadence, accelerometer data, or other data. From this data, some features of or parameters relating to the workout may be derived, such as calorie burn, METs, speed, distance, etc., e.g., by the electronic device 508, interface device 506, and/or module 502, and this data and information may be stored. Even if no specific data relating to the workout can be detected by the module 502 (such as step count, heart rate, etc.), transmission of the room or locale identification data to the electronic device 508 (optionally through the module 502) can be useful to the user, e.g., to provide an indication and some record that a workout has taken place and optionally at least some data indicating the type of workout (which data and information may be entered into and included in the user's workout history).

Figure 8:
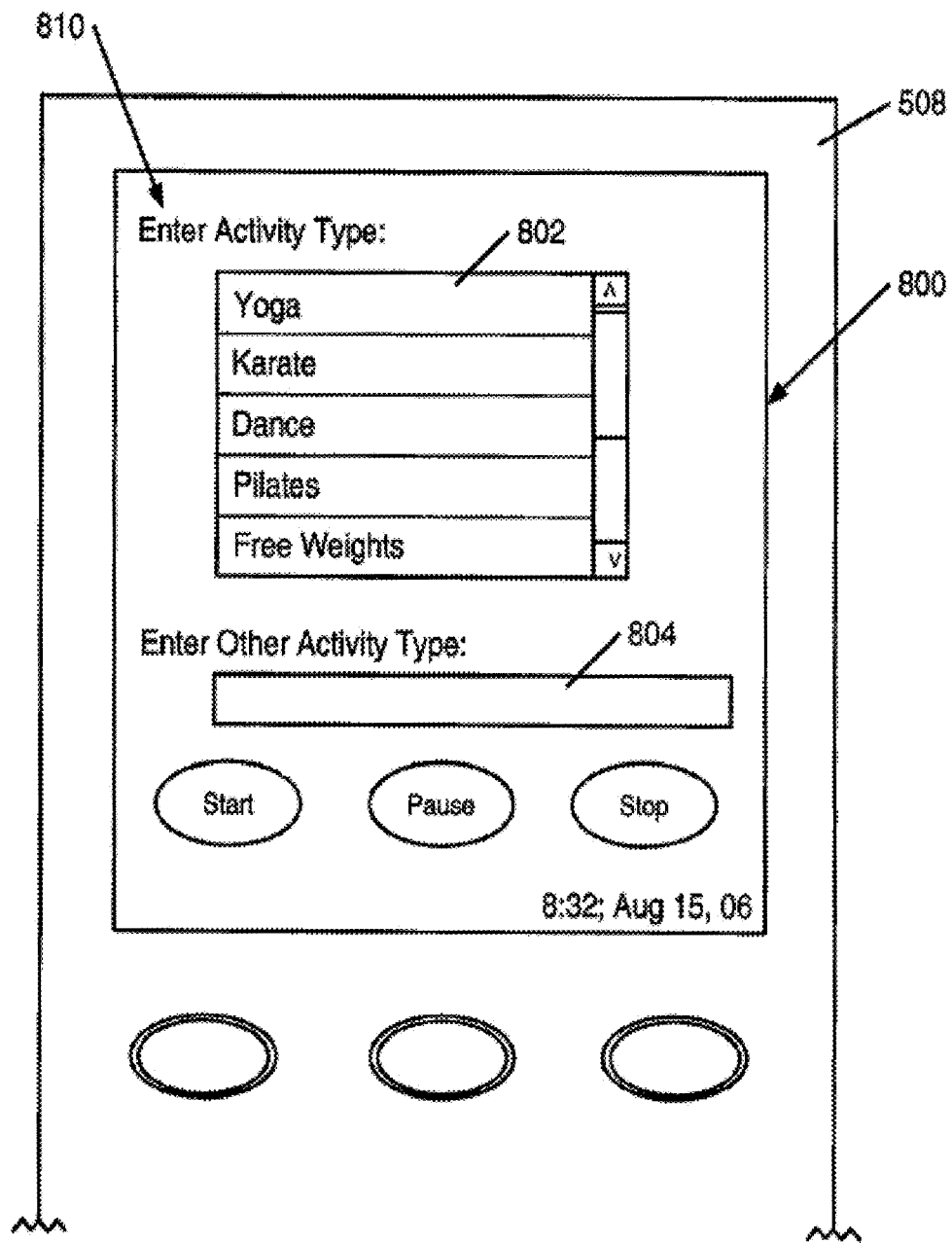
FIGS. 8-19 illustrate various example features that may be provided in and/or controlled by user interfaces of athletic performance sensing systems according to at least some examples of this invention.

Workout information can be entered into the electronic device 508 even in situations where there is no machine, room, or other locale 604 from which to transmit data and/or even in situations where the module 502 (or interface device 506 or electronic device 508) cannot sense data relating to the workout (e.g., when running, jogging, or walking outside; when participating in dance, aerobics, or other classes; martial arts training; free weight lifting; team sports (such as baseball, softball, basketball, football, soccer, etc.) etc.). The data may be provided, for example, by manually entering workout information into the electronic device 508. FIG. 8 shows an example of the electronic device 508 with a display screen 800 having an example user interface 810 allowing user input of information relating to a workout or activity in this situation. While a wide variety of information and combinations of different types of information may be entered, this example interface 810 includes a panel 802 through which the type of activity to be conducted may be selected from a listing and another panel 804 through which the type of activity may be entered (e.g., optionally activities not found in the panel 802). In addition, this user interface 810 includes "start," "stop," and "pause" buttons that allow users to record time and/or timing information associated with the workout or activity, if desired. Again, if the sensor included with the module 502 is able to detect at least some data associated with these types of workouts, such as step count, heart rate, pulse rate, or other data, this data may be collected, sent to the electronic device 508, stored, presented on display screen 800, and/or associated with the specific workout. Collection of data in this manner can be useful to provide at least some information for the user indicating his/her complete workout history (e.g., workout dates, attendance, workout lengths, etc.), even when little or no actual workout data from the available sensors can be produced or made available.

Also, any desired manner of inputting data into the interface screen 800 may be provided without departing from this invention, such as a keyboard, mouse, trackball, roller ball, stylus, pen, touch screen, touch pad, rotary input device, etc. Such interface systems and input devices are conventionally known and used in the electronic device art.

Of course, any desired data information or content may be requested and/or entered through the user interface 810 without departing from this invention. As more specific examples, data input can be requested and/or provided on a more granular level than that described above in conjunction with FIG. 8. For example, more detailed information regarding timing, duration, intensity, or other features of the activity may be requested via interface 810, e.g., depending on the activity type, user settings, etc. For example, if the selected activity was "Free Weights" or "Weight Training," the user interface 810 according to at least some examples of this invention may request entry of additional information, such as type of lifting performed (e.g., squats, dead lift, bench press, military press, curls, etc.); number of sets performed; number of repetitions per set; amount of weight lifted per set; etc. Additionally or alternatively, if desired, the weight machine and/or individual weights may include an electronic module (e.g., such as an accelerometer or the like for sensing direction changes and a transmission system (such as an RFID transmitter)) that allows automatic transmission of certain information to the electronic device 508 (optionally through the module 502 and/or interface device 506), such as repetition counters (each up/down movement of the weights), weight information per set, number of sets, etc. The transmission system may be activated automatically, manually, or semi-automatically.

Systems and methods according to examples of this invention may provide a wide variety of useful information, features, and/or data for users. For example, systems and methods according to examples of this invention allow users to store and retrieve data relating to one or more workouts, which may be stored, for example, on a local computer 702, the remote system 704, on portable devices 502, 506, and/or 508, etc. Any of the sensed data, timing information, and the like may be stored, retrieved, and further processed and analyzed by users. Systems and methods according to at least some examples of this invention further may allow users to compare their workout routines, data, and/or fitness level to other information, such as: their own stored workouts; stored workouts of other users of remote system 704 (optionally workouts of specific individuals, such as friends, workout partners, etc.; users of the same or similar size, weight, age, gender, fitness level, etc.; etc.); similar workouts of well known athletes or celebrities; and the like. As additional examples, if desired, systems and methods according to at least some examples of this invention may further allow users to compare their workout routines, data, and/or fitness level to information related to athletic events in which they may or may not have participated, such as road races, bicycling events, triathlons, etc. (e.g., "where would today's time have finished in last year's Marine Corps Marathon," "how do I compare with the speed of last year's Tour de France winner," etc.).

Systems and methods according to at least some examples of this invention also may be used to provide and/or suggest workouts for users (e.g., pre-programmed workouts, optionally taking into account various factors, such as user age, height, weight, fitness level, gender, past performance, goals, etc.). Such workouts may be designed by fitness experts, e.g., for individual users, for general categories or groups of users, etc. The workouts or information relating to the workout may be downloaded to the portable electronic device 508 (e.g., via computer 702, from remote system 704, etc.), and they may be designed to provide information to the user before the workout begins and/or as the workout progresses, optionally in real time. For example, the downloaded workout may provide a wide variety of information to the user, such as: real time workout parameter feedback (e.g., speed, distance covered, stair-stepping, elliptical, or other rate information, calories burned, elapsed time, etc.); workout activity or machine change information (e.g., when to move to a new machine or activity: "you are done on the treadmill, move to the stationary bike for 20 minutes;" machine setting change information (e.g., to be performed manually or automatically); etc.); real-time comparison information to previous workouts or to a user's "personal best;" etc.).

Moreover, the downloaded and/or presented information on electronic device 508 is not limited to workout information. The electronic device 508 also can provide warnings or reminders (e.g., proper warm-up or cool-down reminders, particularly when abrupt changes in activity are sensed (e.g., by module 502), etc.; over-training warnings (e.g., by comparing workouts on consecutive or recent dates); nutritional reminders; etc). Also, because systems and methods according to at least some examples of the invention can store information regarding workouts performed by a user over time, they can recognize a user's preferences and provide customized workouts or suggest certain workouts or portions thereof, so that the user's workout routine will change (to help prevent boredom) and help him/her better accomplish their goals. Systems and methods according to at least some examples of this invention may be programmed and adapted to provide user rewards over time, e.g., based on continued usage, attaining pre-set goals, etc. Any type of reward may be provided, such as presents, prizes, coupons, discounts, motivational audio or video content, etc., as will be described in more detail below.

Because at least some portions of systems and methods according to examples of this invention may receive data from multiple users, users can compete against one another and/or otherwise compare their athletic performances, even when the users are not physically located in the same area and/or are not competing at the same time (e.g., virtual races or competitions). These features can help motivate users and keep their workout routines interesting. Moreover, systems and methods according to at least some examples of this invention can suggest new workout programs to a user based on workout programs followed by other users (whether or not the "other users" are known by the original user), optionally programs followed or practiced by other users of similar size, weight, or age; the same gender; the same general fitness level; etc. Such features can motivate users to compete with and/or beat their friends or other users at various different workout routines. Changing workout routines also can help users more quickly improve, reach their goals, break through "plateaus," etc.

While various aspects of the invention described in this sub-section are described as providing data and information to/from the portable electronic device 508, those skilled in art will recognize that the data and information may be transmitted to/from other devices without departing from this invention, such as the module 502, the interface device 506, a user's PC or other input device or exercise equipment 604 or 702, etc.

Figure 9:
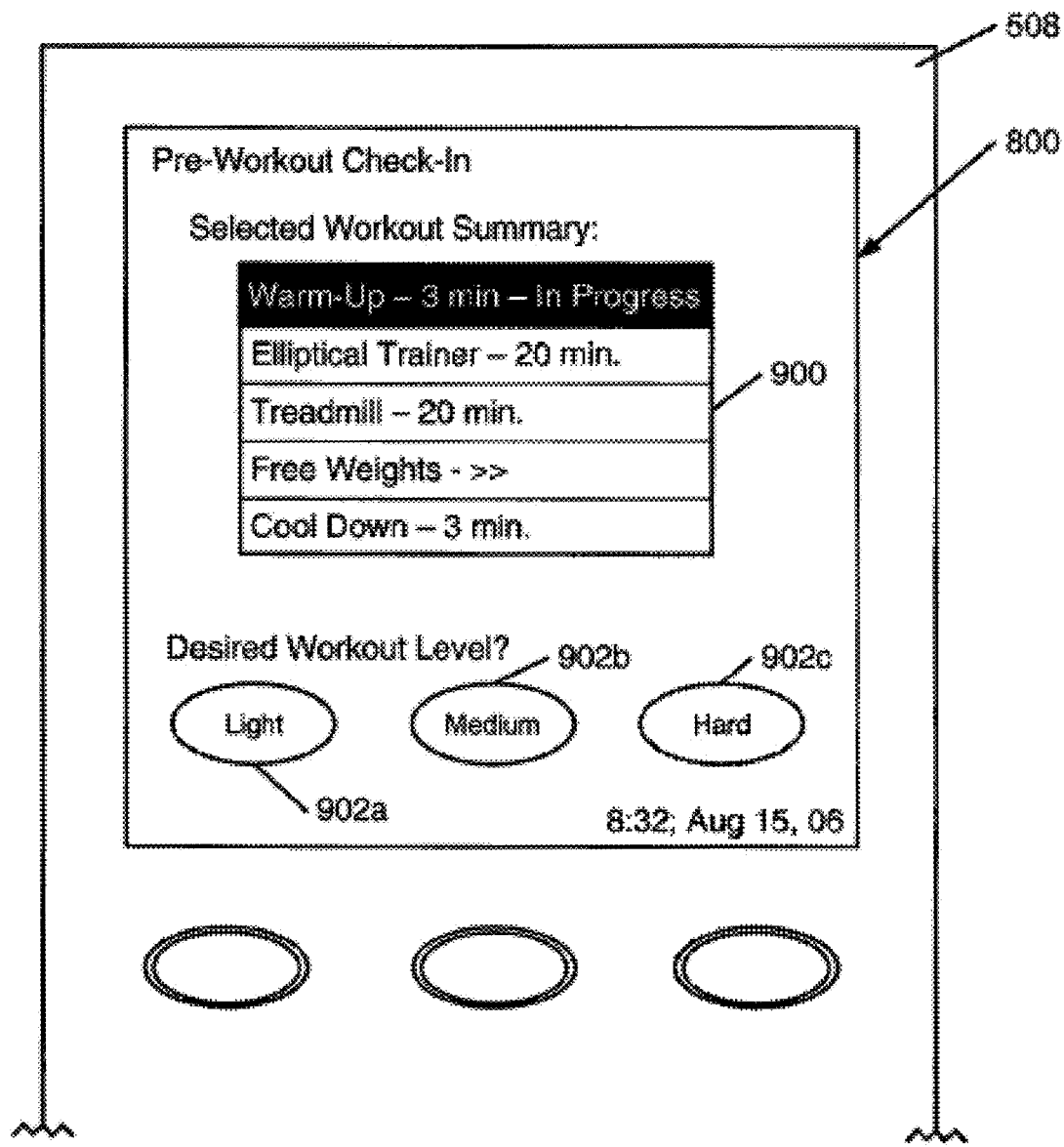

IV. Use of Subjective User Input and/or Feedback in Systems and Methods According to Examples of this Invention Systems and methods according to at least some examples of this invention utilize user feedback or user input in various ways, e.g., to better customize workouts; to change or improve the workout entertainment and/or motivational content; to maintain workout "freshness;" etc. FIG. 9 illustrates one example of systems and methods in accordance with this invention in which user feedback is used to select one or more features of a workout before it begins and/or at the early stages of the workout routine. As shown, in this example, the screen 800 of electronic device 508 displays the general features of a selected workout (e.g., the individual workout activities) for that workout session in panel 900. At some time toward the beginning of the workout (e.g., either before actually starting, during, or after an initial warm-up period, etc.), the user is prompted to enter information indicating how he or she "feels" that day. More specifically, in this illustrated example, as the warm-up period begins or progresses (as indicated by the darkened time slot in the workout schedule shown in display panel 900), the system and method of this example ask the user to input information regarding the desired workout level for that day (e.g., input buttons 902a, 902b, and 902c are provided allowing a user to indicate whether a "light," "medium," or "hard" workout, respectively, is desired for that day). Any number of potential choices for the workout level may be provided without departing from this invention. Optionally, this user interface may be displayed to the user along with motivational, coaching, and/or warning media content, as will be described in more detail below (e.g., audio content encouraging the user to select a hard workout level, a reminder of the past workout, etc.).

The characteristics or parameters of the workout may be varied widely, depending at least in part on the selected workout level. For example, if desired, the types of activities included as part of the workout may be changed, depending on the selected workout level. As another example, the time duration(s) of one or more of the activities may be changed, depending on the selected workout level. As yet another example, if desired, one or more of the amount of resistance, timing/pace/distance goals, calorie burn goals, overall workout times, incline levels, number of free weight lifting sets, number of repetitions per set, free weight lifting weight levels, and the like, may be varied to increase or decrease the "workout level." Also, various combinations of the potential changes described above (as well as other potential changes) may be used to change the "workout level" for the user based, at least in part, on the user's input regarding the desired workout level. Also, any desired amount of increase or decrease in the workout level may be made without departing from this invention. If desired, systems and methods according to this example of the invention may allow more detailed user input indicating the workout level parameters, including user input selecting the various parameters or goals for individual activities and/or the overall workout.

If desired, systems and methods according to at least some examples of this invention may allow users to "drill down" to view (and potentially change) more information regarding a particular workout or activity. For example, if desired, the user could one of the identified workout activities (e.g., treadmill), which action could open another user interface/input panel identifying additional information regarding that activity (e.g., treadmill speed, treadmill incline, treadmill pre-set program information, etc.). If desired, the user may be able to modify more detailed aspects of an individual workout or activity, e.g., through such additional user interface/input panels or in other manners. Any desired number of "drill down" panels and/or levels for accepting user input may be provided without departing from this invention.

Selection and/or modification of a user workout based on subjective user input are not limited to the pre-workout, pre-warm-up, and/or early workout stages. Rather, systems and methods according to some examples of this invention may periodically prompt users to indicate how they "feel" and/or to indicate whether the workout parameters should be changed in some manner. These prompts may occur automatically at various different times during a workout or activity, e.g., at predetermined intervals; at predetermined times into a workout or activity; when the system senses excessive user difficulty in "keeping up" with the workout; when the system senses that the user is too easily keeping up with the workout (e.g., based on pulse or heart rate data, etc.); when a user potentially could exceed his/her personal best, reach a goal or milestone, etc.; etc. Such features can help motivate users and help them more quickly increase their fitness level and/or reach their fitness goals while helping to avoid soreness and over-training (and potentially discouraging) the user.

Figure 10:
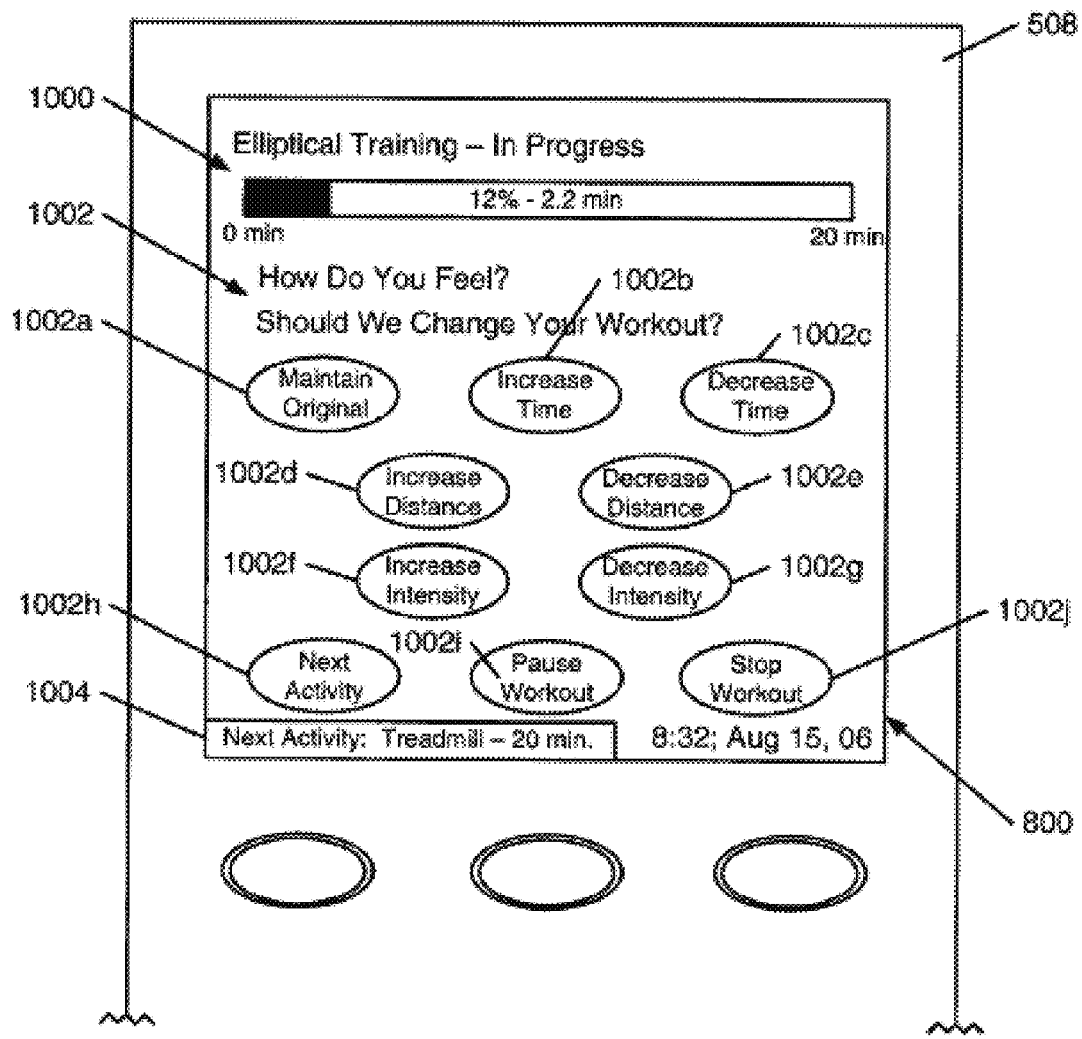

FIG. 10 illustrates an example of the display screen 800 of electronic device 508 providing an example user interface in which the user is prompted to provide feedback during the course of a workout activity. As shown, progress panel 1000 shows the user their current workout activity (elliptical training in this example) and the degree to which this activity has been completed (12% completed, in this example). At this time in this example workout, the system has prompted the user for their subjective feedback (area 1002), asking the user whether the workout should be changed. In this illustrated example, the user interface area 1002 provides input buttons indicating several options for the user, namely: maintaining the original workout activity parameters 1002*a*; increasing the workout activity time goal 1002*b*; decreasing the workout activity time goal 1002*c*; increasing the workout activity distance goal 1002*d*; decreasing the workout activity distance goal 1002*e*; increasing the workout activity intensity 1002*f*; decreasing the workout activity intensity 1002*g*; changing to the next activity 1002*h* in the selected workout routine (the next type of activity is indicated in the interface area 1004 as a "treadmill" workout activity); pausing the workout 1002*i*; or stopping the workout 1002*j*. Any desired information, change options, and the like may be included in the user interface area 1002 and/or information like that described above may be made available through plural input screens without departing from this invention. Also, if desired, this user interface screen may be presented with appropriate motivational, coaching, and/or warning information (e.g., an audio or video clip encouraging the user to increase his/her level, etc.).

Figure 11:
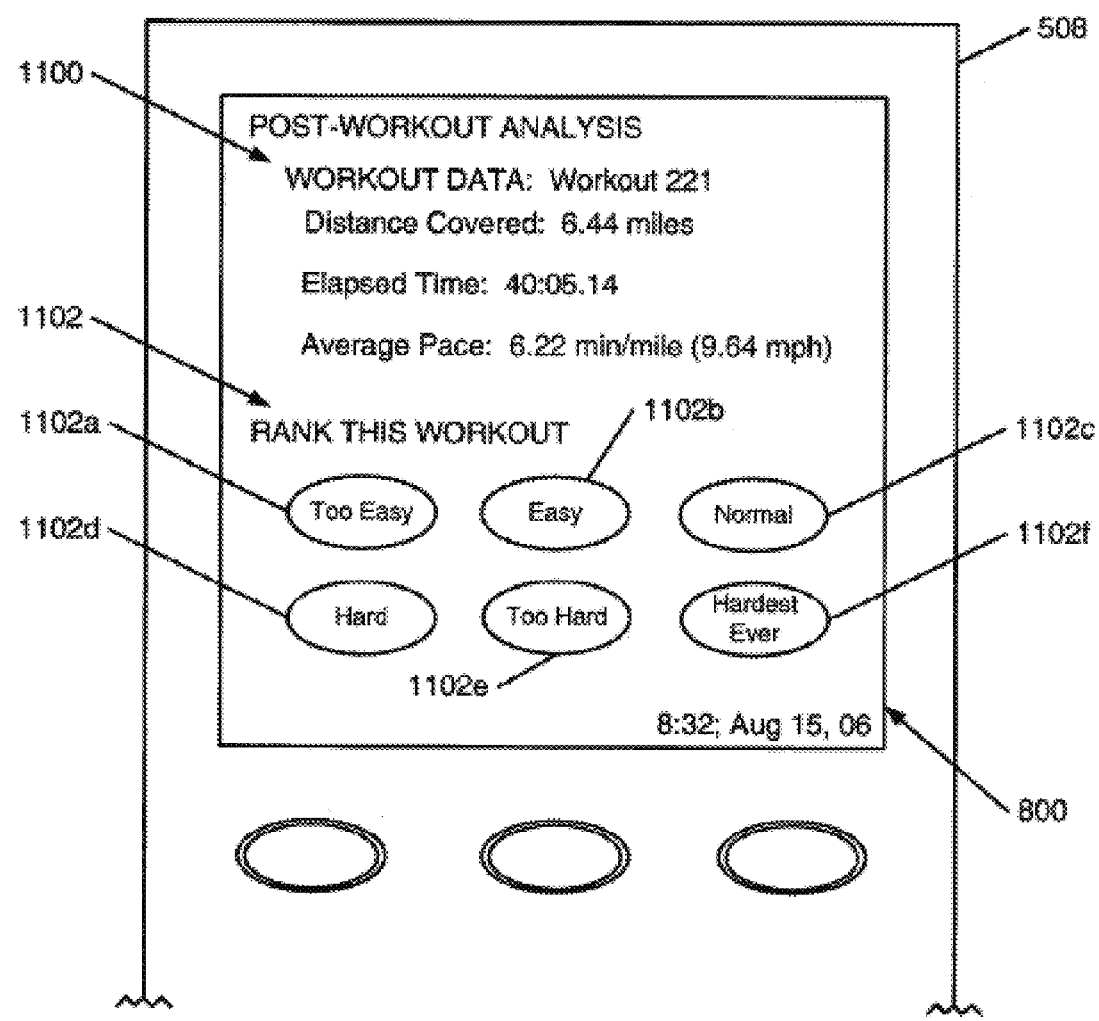
Figure 12:
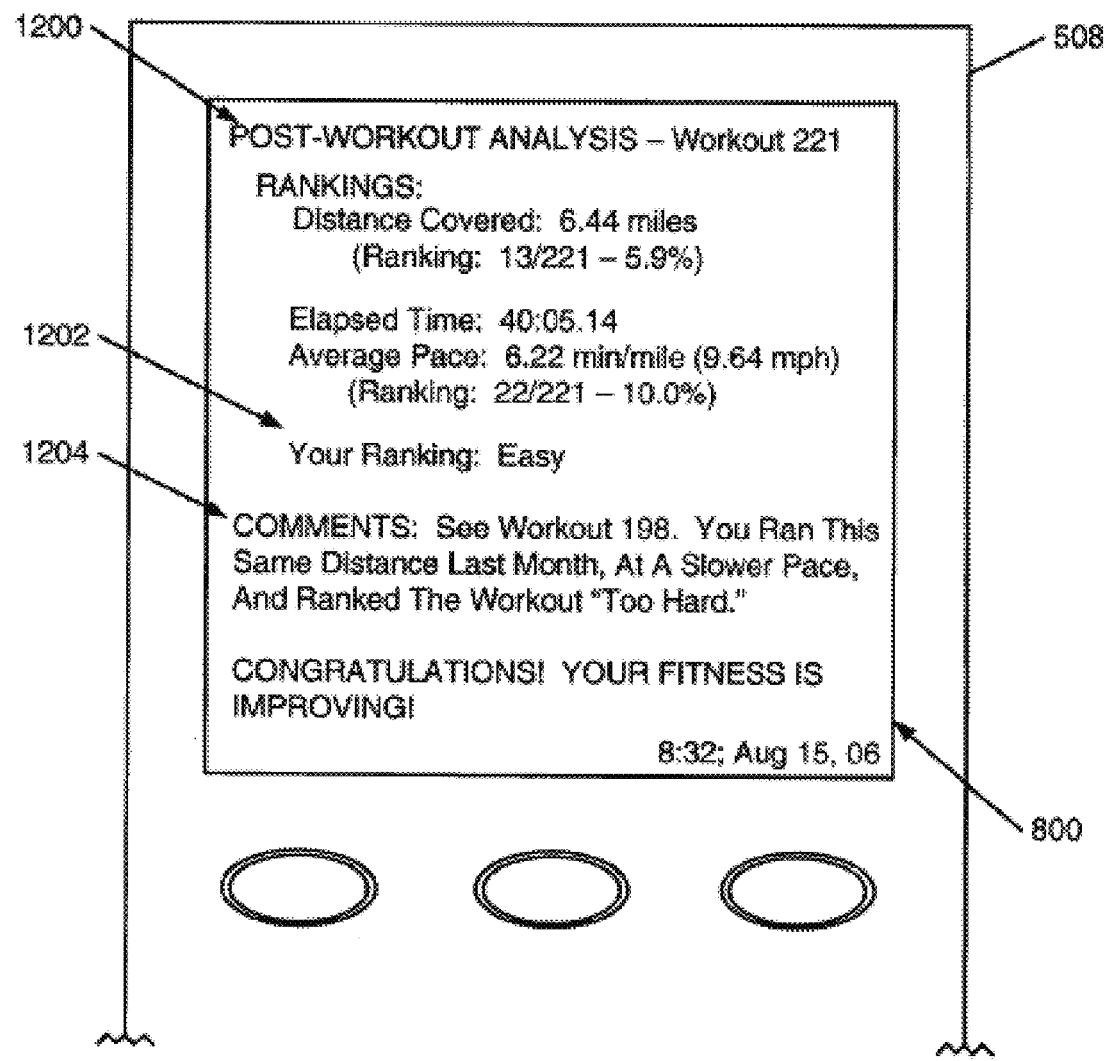

Subjective user input also may be received and used by systems and methods according to at least some examples of this invention after the workout is completed. FIGS. 11 and 12 illustrate examples of user interface screens that may be used in post-workout analysis situations. For example, as shown in FIG. 11, once a workout is completed, systems and methods according to at least some examples of this invention may be programmed and adapted to provide workout information to the user on display screen 800. In this illustrated example, a workout summary area 1100 is provided, indicating various features of the workout, such as: a workout identification code ("Workout 221" in this example); "distance covered" data; "elapsed time" data; and "average pace" data. Any type of data or information may be provided in the workout summary area 1100 without departing from this invention, including user physical or physiological data, etc. Additionally, if desired, workout summary data may be provided for each individual activity or segment included in the workout (e.g., treadmill, elliptical training, weight-lifting, etc.), and the type of data provided for the various different activities may be the same or different (e.g., workout summary data may be different for treadmill workouts as compared with other workouts, such as stationary bicycle, elliptical training, stair-stepping machines, outdoor running, rowing, etc.). Scroll bars, additional display screens, and/or other ways of providing additional information in workout summary area 1100 may be provided in order to allow inclusion and/or presentation of information beyond that which will fit within area 1100 on the electronic device 508.

FIG. 11 further shows a subjective user input area 1102 on the display screen 800 associated with this post-workout analysis. More specifically, systems and methods according to this example of the invention request that the user "rank this workout" using subjective user input area 1102. While any desired rankings and/or potential options may be made available for the subjective user rankings without departing from this invention, in this illustrated example, the user has six choices for ranking the workout, namely: "too easy" 1102*a*, "easy" 1102*b*, "normal" 1102*c*, "hard" 1102*d*, "too hard" 1102*e*, and "hardest ever" 1102*f*. Advantageously, in at least some examples of systems and methods according to this invention, this subjective ranking capability (e.g., ranking area 1102) will be provided to the user on the portable, user carried electronic device 508 immediately upon completion of the workout, so that the true subjective feel and effects of the workout are immediately fresh on the user's mind.

The subjective data may be used in a variety of ways by systems and methods according to examples of this invention. For example, once a subjective user ranking is received in the ranking area 1102 of FIG. 11, an additional post-workout analysis screen 1200 (e.g., as illustrated in FIG. 12) may be provided. This post-workout analysis screen 1200 uses the subjective ranking information and compares the actual parameters of the present workout with objective historical data relating to the same or similar workouts in order to provide feedback to the user regarding this workout, their fitness level, and/or their progress in reaching a pre-set goal. As shown in FIG. 12, in this example, the user ranked the workout as "easy" (area 1202). The post-workout analysis of systems and methods according to this example of the invention compares this workout to other workouts. While any desired parameters may be compared, in this illustrated example, the objective overall distance covered and average pace data for the present workout were compared and ranked with the objective data from previous workouts (optionally, from workouts having the same or similar conditions and/or parameters, workouts including at least some of the same activities, etc.). Additionally, in this example, the subjective user data was used to provide feedback (in the form of "Comments" in area 1204) indicating how the subjective ranking of this workout compares to earlier workouts. Any type of commentary and/or other information may be provided in area 1204 (or in some other manner, such as via audio, via email, etc.), e.g., coaching feedback; motivational or congratulatory feedback; reward information (e.g., a coupon or code for receiving a discount on athletic equipment or clothing, etc.); etc. The subjective feedback also may be used by systems and methods according to at least some examples of this invention to automatically modify future workouts for users, e.g., increase one or more workout parameters (e.g., distance goals, time goals, intensity or resistance level settings, etc.) for workouts indicated as "easy" or "too easy," decrease one or more workout parameters for workouts indicated as "too hard" or "hardest ever," and/or to otherwise modify workouts so as to continue challenging and motivating users while preventing overtraining, soreness, discouragement, etc.

Comparison of subjective and/or objective workout data is not limited to comparisons with efforts made by the individual user and/or historical data generated by the individual user. As described above in conjunction with FIG. 7, systems and methods according to at least some examples of this invention may communicate with remote systems (e.g., over the internet or other network connection), and multiple users may send their workout data to the same remote system(s). Therefore, the user input subjective data, as well as the objective data, relating to a user's workouts may be compared to workout data and/or subjective input generated by others. In this manner, the systems, methods, and/or users can compare their workouts and fitness to other users, such as specific individuals (e.g., their friends, relatives, etc.); famous athletes or celebrities; other users of similar body type or other characteristics (e.g., the same gender; the same or similar age, height, weight; the same general fitness level; etc.); etc. Also, systems and methods according to some examples of this invention may provide completely new workouts for an individual, e.g., based on the user's subjective workout feedback; "borrowing" workouts of others saved in the system (e.g., people performing similar workouts, people of similar age, height, weight, fitness level, etc.); etc. Multiple users may participate in virtual races or other fitness competitions (e.g., first to run 100 miles, first to lift 5000 lbs., etc.), which can help keep users motivated and improve their fitness. Such virtual races or competitions also may be designed to have a charitable beneficiary, e.g., in which users obtain pledges for monetary support for every mile run, or the like, akin to actual (non-virtual) road races used to raise money for charity.

V. Use of Music and Other Content in Systems and Methods According to Examples of this Invention Aspects of this invention further relate to the use of music and/or other audio and/or video content in athletic performance sensing and/or tracking systems. Such content may be useful in a variety of ways in systems and methods according to examples of this invention, e.g., for providing entertainment, information, coaching tips or reminders, motivational content, etc. Advantageously, in accordance with at least some examples of this invention, in addition to being able to download workout routines and/or data as described above, electronic device 508 will constitute or include an audio and/or video presentation device that allows users to also play and/or download music, videos, or other audio/video data for presentation during the course of a workout (e.g., a radio, a tape player, an MP3 player, an IPOD® device (commercially available from Apple Computer, Inc., of Cupertino, Calif.), etc.).

While the audio or video presentation device may be used in a conventional manner, e.g., with user controlled content and/or output during the course of a workout, systems and methods according to at least some examples of this invention allow more user interaction and control over the content presentation provided during the workout. For example, systems and methods according to at least some examples of the invention may allow users to pre-program and/or "mix" their own workout with audio/video and/or other content, e.g., to include desired audio/video content (e.g., music playback, video playback, coaching or motivational content, etc.) at desired times and in a desired timing or relationship with respect to various different phases of a workout routine or exercise program. Plural workout routines, optionally user mixed workout routines, stored and downloaded workout routines (optionally including pre-selected or user selected music), purchased workout routines (optionally including pre-selected or user selected music), and the like, may be stored on or downloaded to the electronic device 508. Also, in systems and methods that utilize an output device, a networked connection, or other computer base station or remote station, users may make their pre-programmed workouts available to others (e.g., "publicly available" or otherwise selectively available to one or more other individuals on the system), e.g., for downloading over the network or otherwise transmitting to another user's electronic device 508.

Figure 13:
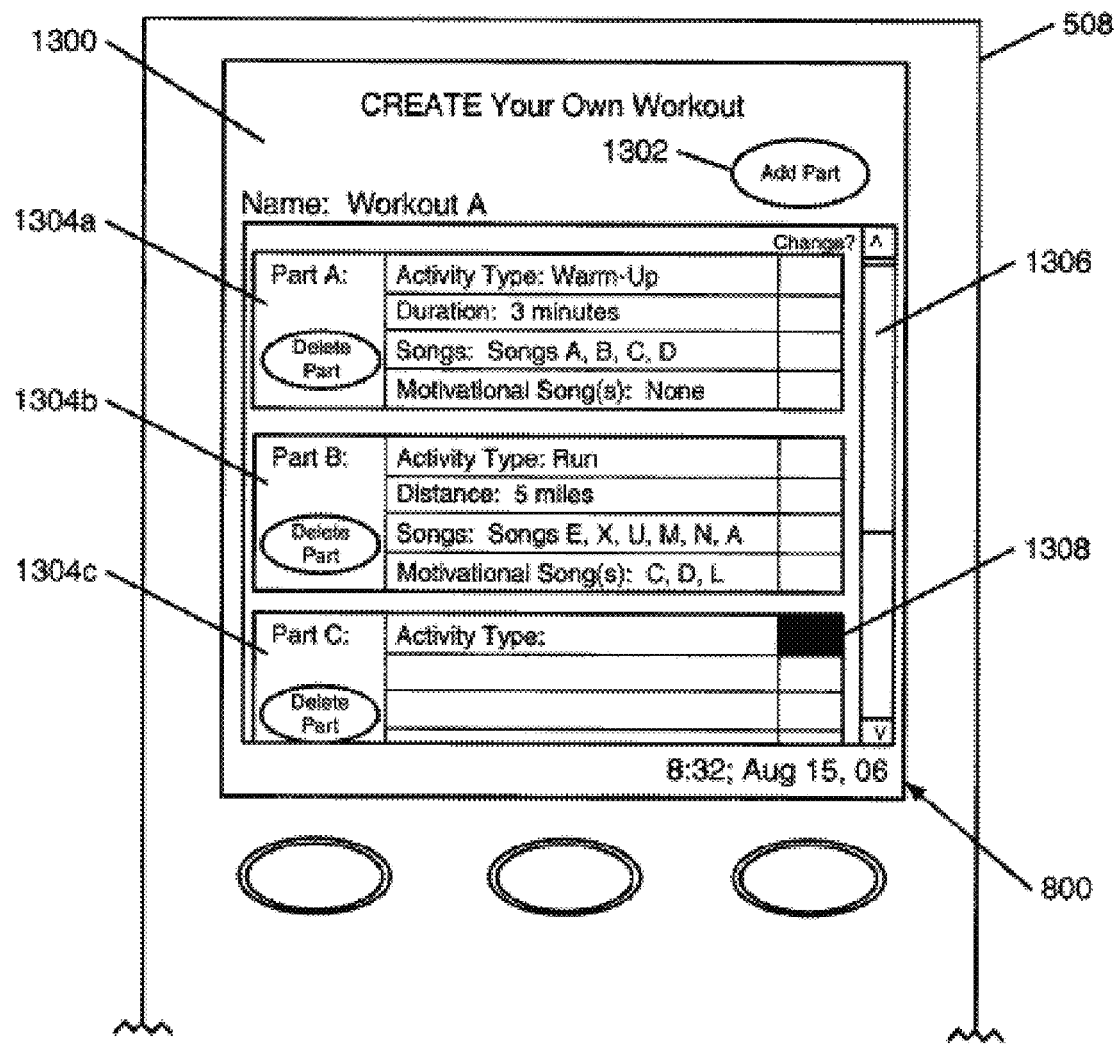
Figure 14:
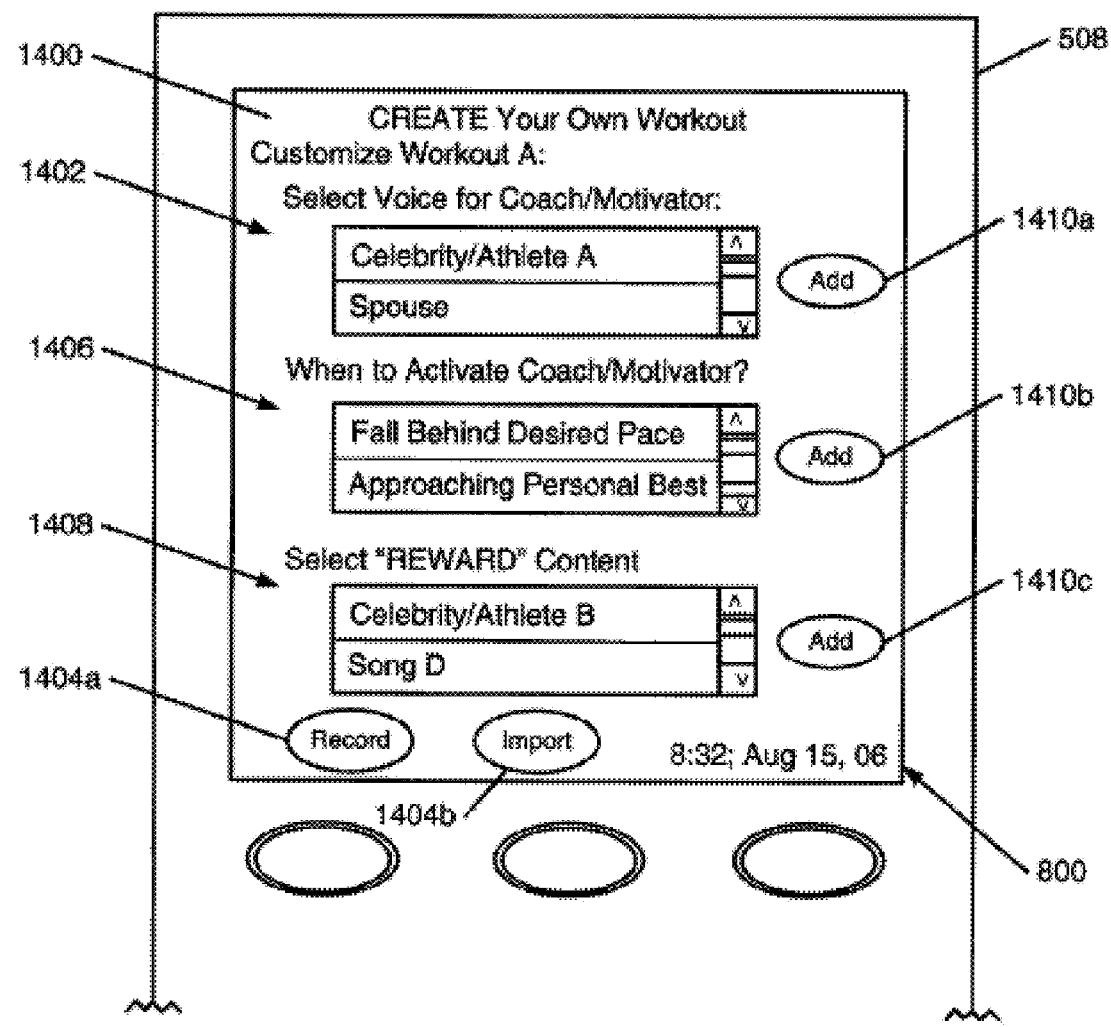

FIGS. 13 and 14 illustrate example features of user interfaces that may be used to allow users (or others, such as coaches, trainers, etc.) to create their own customized workout routines (e.g., for their own use, for use by others, etc.). While these figures illustrate providing the user interface and creating a workout routine using electronic device 508 for user input, those skilled in the art will understand that any computer in communication with the overall system (e.g., via the internet, via a wired connection, etc.) may be used for creating the workout routine without departing from this invention, such as personal computer 702 and/or another computer in communication with the electronic device 508 and/or remote system 704 from FIG. 7. Also, while particular user interface elements are shown and described in conjunction with FIGS. 13 and 14 (e.g., scroll bars, input regions, etc.), other user interface elements, user input hardware, and/or ways for receiving user input to create and/or change features of the workout routine may be used without departing from the invention.

User created workout routines according to examples of this invention may include one or more "parts," wherein a "part" constitutes a specific type of workout activity, such as: warm-up, walking, running, biking, rowing, use of exercise equipment or gym machines (such as treadmills, stair-stepping machines, elliptical machines, exercise bicycles, rowing machines, cross-country ski simulators, etc.), weight lifting (free weights or gym machines), yoga, dance, aerobics, martial arts, team sports, cool-down, etc. In this example system and user interface, any combination of activities may be included in a workout routine without departing from this invention, including, for example, gym or spa based activities, outdoor or free range activities, machine or free (non-machine) based activities, team sports or individual activities, etc.

In accordance with examples of this invention, as illustrated in FIG. 13, a user can begin creating a workout by selecting the "Add Part" button 1302 on user interface 1300, to add a distinct "part" or activity to the workout routine. In this example system and interface, adding a "part" or activity to the workout routine creates a "part" or activity block 1304a, 1304b, and 1304c. While three activity blocks 1304a, 1304b, and 1304c are illustrated in FIG. 13, any number of activity blocks may be included in a workout routine, and other blocks relating to the workout routine may be viewed, for example, by interacting with scroll bar 1306 or otherwise indicating a desire to see other parts of the workout routine.

Once a part or activity block is created, it may initially appear blank or with a line for the "activity type" provided (see "Part C" in activity block 1304c in FIG. 13). A user then may select the desired activity type. For example, as indicated in FIG. 13, after adding the part or activity block 1304c, in this example interface 1300, the user may indicate a desire to add or change the "activity type" by selecting the "change" block 1308 associated with the Part C "Activity Type" line. This action may cause a list of possible "activities" to appear (e.g., as a "pop-up," as a separate screen, as an overlay, etc.), and the user may select the desired activity for the workout from the list, e.g., using any of a variety of user interface elements and interaction mechanisms and methods, as are known and used in the art.

After the activity type is selected, other lines of the activity block may be filled in, optionally in a user changeable manner. The selected activity type may affect the data or information to be filled in and/or included in the remainder of the input lines for the "part" or activity. For example, selection of an activity type that utilizes an exercise machine may populate other lines of the part 1304a, 1304b, and/or 1304c to include information relevant to that machine, such as desired speed, desired incline level, desired weight or other resistance levels, other desired workout intensity features, desired distance, desired calorie burn, desired distance traveled, desired total elapsed time, desired machine settings (such as hill, random, etc.), etc. If desired, systems and methods according to at least some examples of this invention may allow users to even more finely customize the workout routine, e.g., by providing the ability to control and/or change the desired parameters of a workout over time during a given activity (e.g., change hill, resistance, or intensity levels of a machine over time, change running speed over time, etc.). While the additional lines of a given "Part" 1304a, 1304b, and/or 1304c may be populated with default settings, e.g., when the part and/or activity type are/is initially selected, systems and methods according to at least some examples of the invention may allow users or others to freely customize and/or change the content of these lines, e.g., in any desired manner, including, if desired, in the general manners described above for changing the "activity type." Optionally, if desired, the default settings, if any, may be determined based on any desired information, including, for example, historical data relating to a user's recorded workout history in general, a user's workout history for that particular activity type, or other features of a user's preferences or history (such as typical overall workout elapsed time, elapsed distance, typical speed, typical incline or resistance settings, weight, age, weight loss/gain, etc.).

As illustrated in FIG. 13, data input creating and relating to the various workout parts 1304a, 1304b, and 1304c includes "Songs" (or optionally other media or other content) that may be presented to the user during the course of that part of the workout. When the electronic device 508 is a media playback device (such as an MP3 player, an IPOD® 0 device (commercially available from Apple Computer, Inc., of Cupertino, Calif.), etc.), systems and methods according to at least some examples of this invention may play the user indicated list of songs during that part of the workout routine. If desired, song or other media content presentation can be even more specifically targeted to specific times or portions of the workout activity. In these manners, users can selectively and easily control the media content presented during various portions of the workout routine and activities without the need to adjust the settings or output of the device 508 during the course of the workout.

A variety of ways of presenting the media content may be provided without departing from this invention. For example, if desired, systems and methods according to at least some examples of this invention may play back the user indicated songs in the user specified order, in a random or shuffled order, in a continuous looping order, etc. Additionally or alternatively, if desired, the user may include media content in the list or line for that part 1304a, 1304b, or 1304c that will last longer than the allotted time or duration for the activity, and systems and methods according to the invention can be adapted to handle this situation in any desired manner (e.g., by stopping the playback when the activity ends or changes, and optionally resuming the playback from the stopped location or from the interrupted song the next time that workout activity, workout part 1304a, 1304b, or 1304c, or media content list is used, etc.). As yet another potential option, if desired, playback may continue until the next workout activity is undertaken (e.g., as indicated or sensed by module 502, user input, etc.), to continue providing entertainment and/or other content to the user between workout activities. Other desired ways of handling these situations may be used without departing from this invention. Also, if desired, a user may be provided with the ability to override the pre-selected content with new media selections during the course of the workout.

If insufficient media content is specified for an activity's duration, systems and methods according to examples of the invention also may handle this situation in any desired manner without departing from this invention. For example, the specified songs or content may be repeated, new songs or content may be automatically selected (optionally, based on other user input or history, such as from user enumerated "favorites," from most frequently played content, from content with similar characteristic(s) to the user identified content (e.g., content with a similar beat, cadence, etc.; content from the same artist or the same genre; content "borrowed" from other user workouts including this same activity; content "borrowed" from other workout activities within this same workout; etc.). Other desired ways of handling these situations may be used without departing from this invention.

The workout parts 1304*a*, 1304*b*, or 1304*c* of this illustrated example include another feature, namely, a "Motivational Song(s)" line. If desired, users of systems and methods according to at least some examples of this invention may select one or more "motivational songs." The motivational song(s) (or other audio/video media content) may be played at various times during a workout routine, e.g., in an effort to help motivate the user to better or continued performance. For example, when a user of a gym machine approaches a portion of the workout having high intensity (such as high incline, high resistance level, increased speed, etc.), systems and methods according to at least some examples of this invention may automatically output one of the motivational songs (or other media content), in an effort to motivate the user to expend additional effort to meet the additional increased intensity challenge. As additional examples, motivational song(s) may be automatically triggered, for example: when a user approaches a personal best (e.g., best split time, best mile time, longest total distance, etc.); when the user approaches a predetermined time, distance, or location in the workout; when the user falls behind a predetermined pace; when the user approaches a preselected goal or milestone; etc. Any desired time, timing, or other parameters may be used for triggering presentation of the motivational content without departing from this invention (examples of which will be described in more detail below). The motivational content also may include alphanumeric or textual information (e.g., in addition to or in place of audio and/or video content).

As yet another example, if desired, the device 508 (or 506) may include a "motivate" hard button, the user interface may include a "motivate" icon, or the overall system otherwise may make presentation of the motivational content readily available for the user to manually trigger during the workout routine, so that users can easily trigger presentation of motivational songs or other content at will (e.g., if they begin feeling lethargic or otherwise feel they are unmotivated or falling behind their desired output or pace, if they simply decide they want to pick up the pace or need motivation, etc.).

FIG. 14 illustrates additional potential features that may be available for customizing and mixing workouts for users of systems and methods according to at least some examples of this invention. In addition to or as an alternative to the motivational song(s) features described above, systems and methods according to at least some examples of this invention may allow users (or others) to select an audio/video "coach" or other "motivator," if desired, to provide encouragement to the user before the workout, as the workout progresses, and/or after the workout. This content source may be selected, for example, using user interface area 1402 of the interface 1400 shown in FIG. 14 ("add" button 1410*a* allows the user to select one or more of the available options for use as the coach/motivator voice, video, etc.). Any desired audio/video content may be used without departing from this invention, including, for example, voices or video of: a user's coach or trainer; a famous athlete or celebrity (e.g., selected by the user, optionally from external sources, such as the remote source 704 described above in conjunction with FIG. 7; stored in memory on electronic device 508; etc.); a user's spouse; a user's child; the user; etc. If desired, the user interface 1400 also may include user interaction and/or input elements, such as icons or buttons 1404*a* and 1404*b*, that allow users to record or import (from an external source, such as remote source 704 over a network of FIG. 7) any desired audio and/or video content to be used as the coach or motivator content (e.g., the user's child's voice encouraging the parent to really try hard for a strong finish, etc.).

As exemplified by area 1406 of the user interface 1400 of FIG. 14, a wide variety of options and/or situations may be made available for automatically triggering or activating the coach/motivator content. Any number of different trigger events or situations may be selected by a user and used in a given workout routine or activity without departing from the invention (optionally with some delay between successive activations of the coach/motivator content, e.g., to give the user an opportunity to put forth the additional effort in response to the previous coach/motivator content, to prevent overplaying of the content, etc.). One or more of the user desired triggers may be selected, for example, using "add" button 1410*b*. Also, different workouts or parts thereof may include and use different trigger or activation events, optionally, events selected and determined by the user. Examples of potential triggers for coach/motivator content include: falling behind a predetermined pace (e.g., slowing below an actual trigger pace level, slowing a certain percentage below a base or average pace, etc.); approaching a personal best (or a personal worst); working out for a predetermined elapsed time; reaching a predetermined distance or location; reaching a predetermined number of sets or repetitions; approaching a difficult or intense portion of the workout; falling pulse or heart rate; etc. Also, if desired, systems and methods according to at least some examples of this invention may have automatic or default triggers, optionally triggers that activate in addition to user selected activation triggers. The system need not be designed to trigger coach or motivator content during each triggering event experience, e.g., if doing so would result in over exposure to the coach/motivator content.

If desired, systems and methods according to at least some examples of this invention additionally or alternatively may include and present "reward content" to users. Users may enter and/or control the reward content through area 1408 of this example user interface 1400. Reward content may take on a variety of different forms without departing from this invention, such as an audio and/or video congratulatory statement from a celebrity, famous athlete, spouse, child, coach, trainer, etc. (e.g., similar to the sources of coaching/motivational content described above). Additionally or alternatively, if desired, the reward content may constitute a reward song, e.g., selected by the user, selected from a predetermined list created by the user, etc. Like the coach/motivator content selected through the use of interface area 1402, the content source for the reward content may be selected using any desired user interface system or elements, for example, the "add" button 1410*c*, which allows selection of one or more available options for reward content from a listing. The reward content may originate from any desired source, such as from external sources, like a remote source 704 described above in conjunction with FIG. 7; stored in memory on electronic device 508; etc. If desired, user interaction elements, such as icons or buttons 1404*a* and 1404*b* also may be used to record or import (from an external source, such as remote source 704 over a network of FIG. 7) any desired audio and/or video (or other) content to be used as the reward content. Although not illustrated in FIG. 14, the user interface 1400 also may accept user input to indicate the times and/or triggers for activating the reward content, e.g., for achievement of any type of goal (e.g., running a lap or split time or distance at or faster than a certain pace; increasing the number of weights, sets, or repetitions when weight lifting; increasing incline or resistance levels on exercise machines; increasing total elapsed time or distance in an activity; successfully achieving a goal indicated by the coach or motivator; etc.). For example, an area similar to area 1406 for triggering the coach/motivator content may be used for specifying user selected reward triggers.

While reward content may be presented at the end of a workout or activity, this is not a requirement. Rather, if desired, reward content may be presented at any relevant time during an athletic performance, e.g., for achievement of any type of goal or milestone (e.g., running a lap or split time or distance at or faster than a certain pace; increasing the number of weights, sets, or repetitions when weight lifting; increasing incline or resistance levels on exercise machines; increasing total elapsed time or distance in an activity; etc.). Presenting reward content at various intermediate time periods can serve a dual purpose of additionally providing motivational content to the user. Reward content also may constitute alphanumeric or textual content (e.g., in addition to or in place of audio and/or video content).

Figure 15:
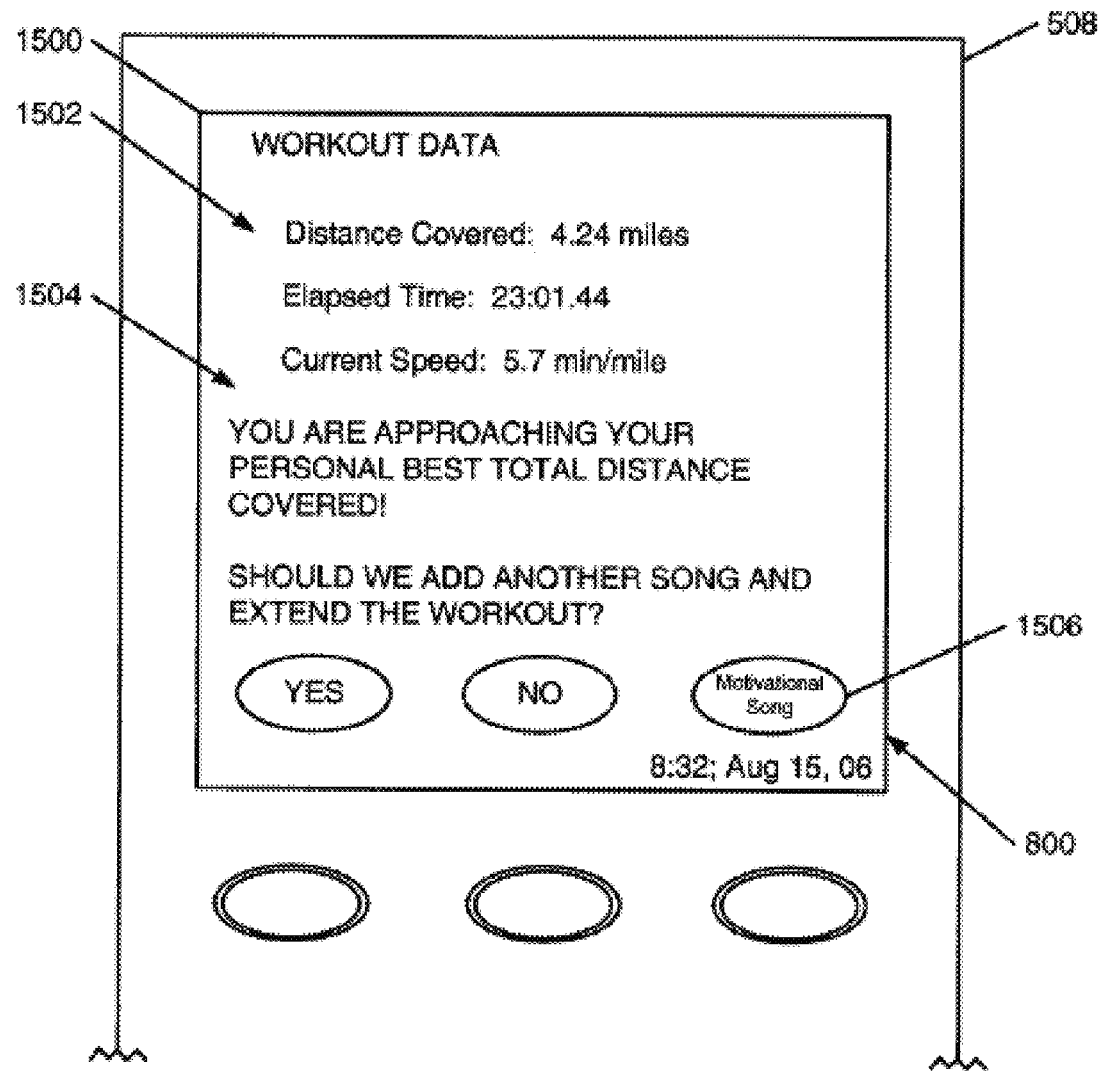

FIG. 15 illustrates an example of use of the display screen 800 of an electronic device 508 for providing a user interface 1500 including motivational content, e.g., to help motivate users to extend their workout, to improve their performance, and/or to attain or exceed their desired fitness goals or personal bests. As a workout routine proceeds in this example system and method, the electronic device 508 receives speed, distance, and timing information and compares this information to past workout data for the user relating to his/her personal bests. In this illustrated example, total distance, elapsed time, and current speed data are displayed to the user in area 1502. In addition, the collected data relating to the existing workout in this example indicates that the user was approaching his/her personal best in total distance covered. Any relevant data may be used to trigger this type of motivational content (e.g., total time, total calorie burn, current pace, etc.).

In such situations, systems and methods according to at least some examples of this invention may prompt the user to increase his/her effort and/or extend his/her workout in an effort to reach a predetermined goal or milestone and/or to set a personal best. Users may be informed of the presence of this prompt on the screen, if desired, using an audio and/or visual indicator, such as a beep, a flashing light or icon, etc. Various types of potential motivational content are described above in conjunction with FIG. 14. Additionally or alternatively, if desired, music (or other audio, video, textual, or alphanumeric content) may be used as a motivator. In the illustrated example, area 1504 of the interface 1500 advises the user that he/she is approaching some goal or milestone. The interface 1500 then encourages the user to extend the workout, e.g., for the length of time represented by at least one additional song. If the user indicates "yes" in response to this prompt, one or more additional songs will be played and the workout may be extended (if "no" is indicated, the workout may continue and end at its originally designated time/distance, etc.). Interfaces of the types illustrated in FIG. 15 may be particularly useful in situation where achieving the identified goal, milestone, or personal best will extend the workout in some manner beyond previously user set workout parameters (e.g., extend the overall time, distance, etc.), e.g., to give the user an opportunity to maintain his/her original schedule, if desired.

FIG. 15 illustrates an additional potential option that may be available in such situations. Rather than simply playing the next song from a listing or randomly selecting a song from those stored on or available through the electronic device 508, systems and methods according to at least some examples of this invention may allow users to designate use of and/or select one of their particularly identified motivational songs during this extended workout period. This may be accomplished, for example, by selecting the "motivational song" icon 1506. This action may automatically select a song from the user's pre-designated motivational song listing (e.g., see FIG. 13), optionally a random selection from that listing, if the motivational song listing includes multiple songs. Alternatively, if desired, interaction with icon 1506 may activate a listing that allows the user to select a specific motivational song desired at that time. Other interfaces and ways of providing a motivational song to the user may be used without departing from this invention.

The motivational song icon or button (or other interface element) 1506 may appear in some or even all screens of the overall systems, methods, and user interfaces according to examples of this invention, if desired. This feature can allow users to have easy access to and activation of motivational content. Additionally or alternatively, if desired, a hard button or other hardware element may be provided with the electronic device 508 (or interface 506 or other device) to allow easy access to and/or activation of the user's motivational content.

Additional examples of user interfaces relating to, features of, and use of motivational songs and motivational song libraries will be described in more detail below in conjunction with FIGS. 16-19.

VI. Use of Subjective User Input Relating to Music and/or Other Content in Systems and Methods According to Examples of this Invention As described above, e.g., in conjunction with FIGS. 13-15, one aspect of systems and methods according to at least some examples of this invention relates to providing entertainment, motivational, and/or reward content (e.g., audio, video, or other media content, alphanumeric or textual content, etc.) to users, e.g., in an effort to keep users from becoming bored and/or to drive users to improve their fitness, achieve their goals, etc. Motivational songs (or other media content) may be used at a variety of different times during a workout, such as when a user has an opportunity to reach a pre-selected goal or milestone; when a user has an opportunity to reach a personal best; when a user actually achieves a goal, reaches a milestone, or sets a personal best; when a user falls behind a pre-selected pace or goal; when a user requests a motivational song; etc.

Figure 16:
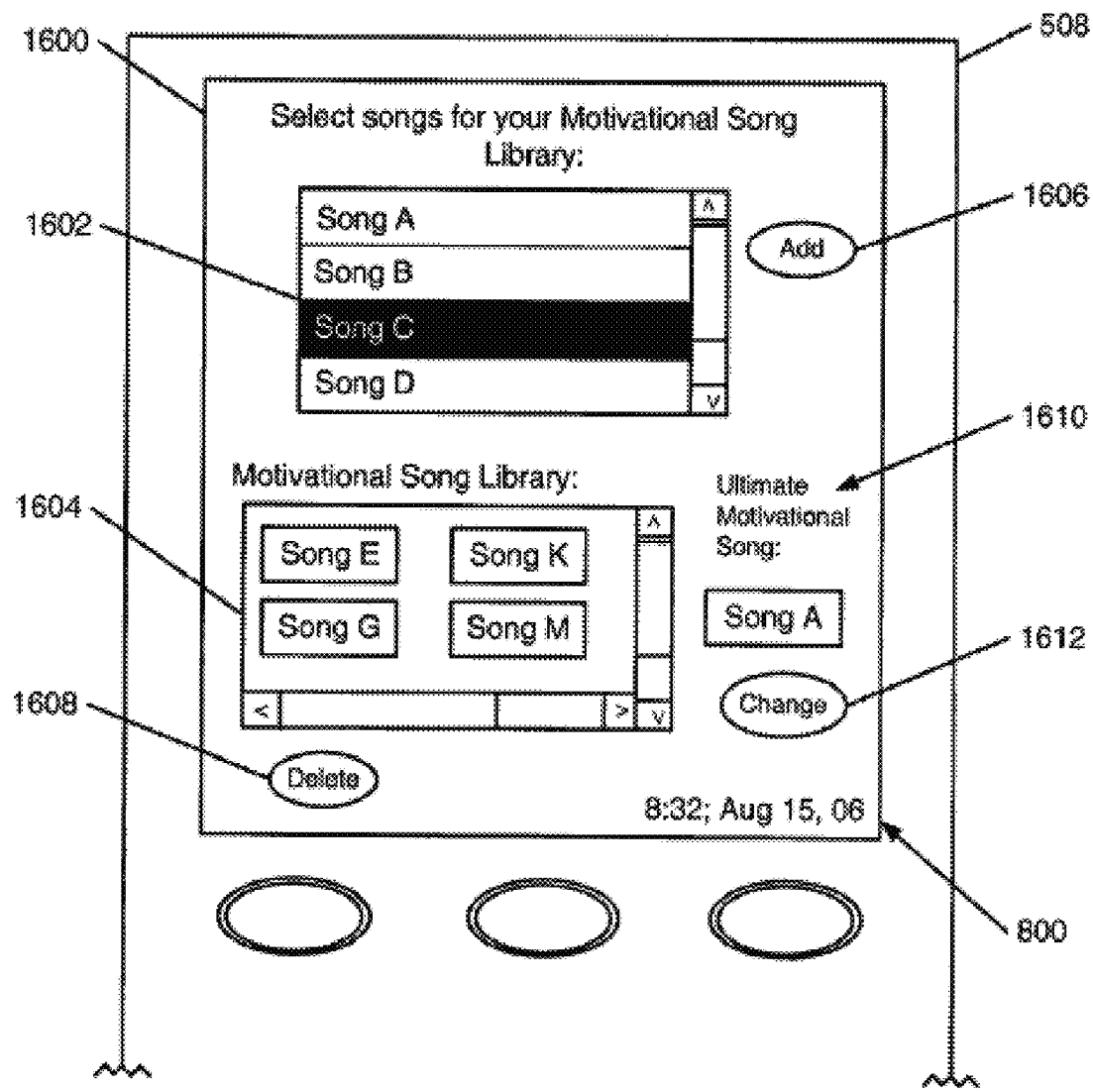

FIG. 16 illustrates an example user interface 1600 through which motivational songs may be selected by users based on their own personal preferences. This user interface 1600 may be made available to users at any desired location, e.g., provided on the electronic device 508, provided on a user's personal computer 702, downloaded from a remote system or source 704, etc. In this illustrated example user interface 1600, activation of the interface 1600 produces a song library listing 1602 through which users can select one or more songs (e.g., highlighted "Song C" in this example) and "add" it/them to the "Motivational Song Library" 1604 using the "Add" button icon 1606. Optionally, if necessary and desired, selection of the "Add" icon 1606 may activate systems, methods, and/or user interfaces to allow users to download and purchase the media content, e.g., from a remote, commercial, on-line source, etc. Songs may be removed from the Motivational Song Library 1604 using "Delete" icon 1608. Many variations in the content of, presentation of, and user interaction with a user interface for identifying and selecting motivational songs and controlling the content of a motivational song library are possible without departing from this invention. Also, while the discussion above (and much of that which follows) describes the motivational content in terms of "motivational songs," those skilled in the art will appreciate that motivational content may take on forms other than songs without departing from this invention, such as any desired audio, video, and/or media content; alphanumeric or textual content; e.g., that may be presented through a user carried portable playback device.

FIG. 16 illustrates another feature that may be available in systems and methods according to at least some examples of this invention. The user interface 1600 of this example requests users to select an "ultimate motivational song" (see area 1610). The ultimate motivational song may or may not be one of the songs included in the motivational song library 1604, and it may be used in a variety of ways. In this illustrated example, the ultimate motivational song may be changed by selection of the "change" button or icon 1612, and then selection of a different song (e.g., from the general listing 1602 or the motivational song library 1604) or vice versa. Other ways of selecting and changing the ultimate motivational song, when present, may be used without departing from this invention.

As noted above, the "ultimate motivational song" potentially may be used in a variety of ways in systems and methods according to examples of this invention. For example, if the "ultimate motivational song" is one of a user's favorite workout songs, its designation as the "ultimate motivational song" may cause it to be used more frequently by systems and methods according to some examples of the invention as opposed to other identified "motivational songs." In such situations and arrangements, the user will hear their favorite song more frequently, but because of the presence of other motivational songs in the library 1604, the ultimate motivational song will not be played in every instance that a motivational song is presented. As another example, the "ultimate motivational song" may be reserved for "special" workout occasions, e.g., when user goals or milestones are potentially within reach, when personal bests can be exceeded, etc., while other motivational songs may be used at other times, such as when a boost is needed, when the user falls below a pre-set pace, etc. As still another example, if desired, the ultimate motivational song may be reserved for use in response to user input requesting the motivational song (e.g., when button or icon 1506 is selected, as described in conjunction with FIG. 15), while the other motivational songs in the library 1604 may be automatically (optionally randomly) selected by systems and methods according to the invention, e.g., in response to (and/or in an effort to enhance) the user's performance. Systems and methods according to examples of this invention may use the ultimate motivational song (if any) in still other ways without departing from the invention.

Optionally, if desired, the motivational song library may be omitted in systems and methods according to some examples of this invention. If desired, a single motivational song may be identified by users (rather than a collection of songs), e.g., to provide motivational and/or reward content.

Figure 17:
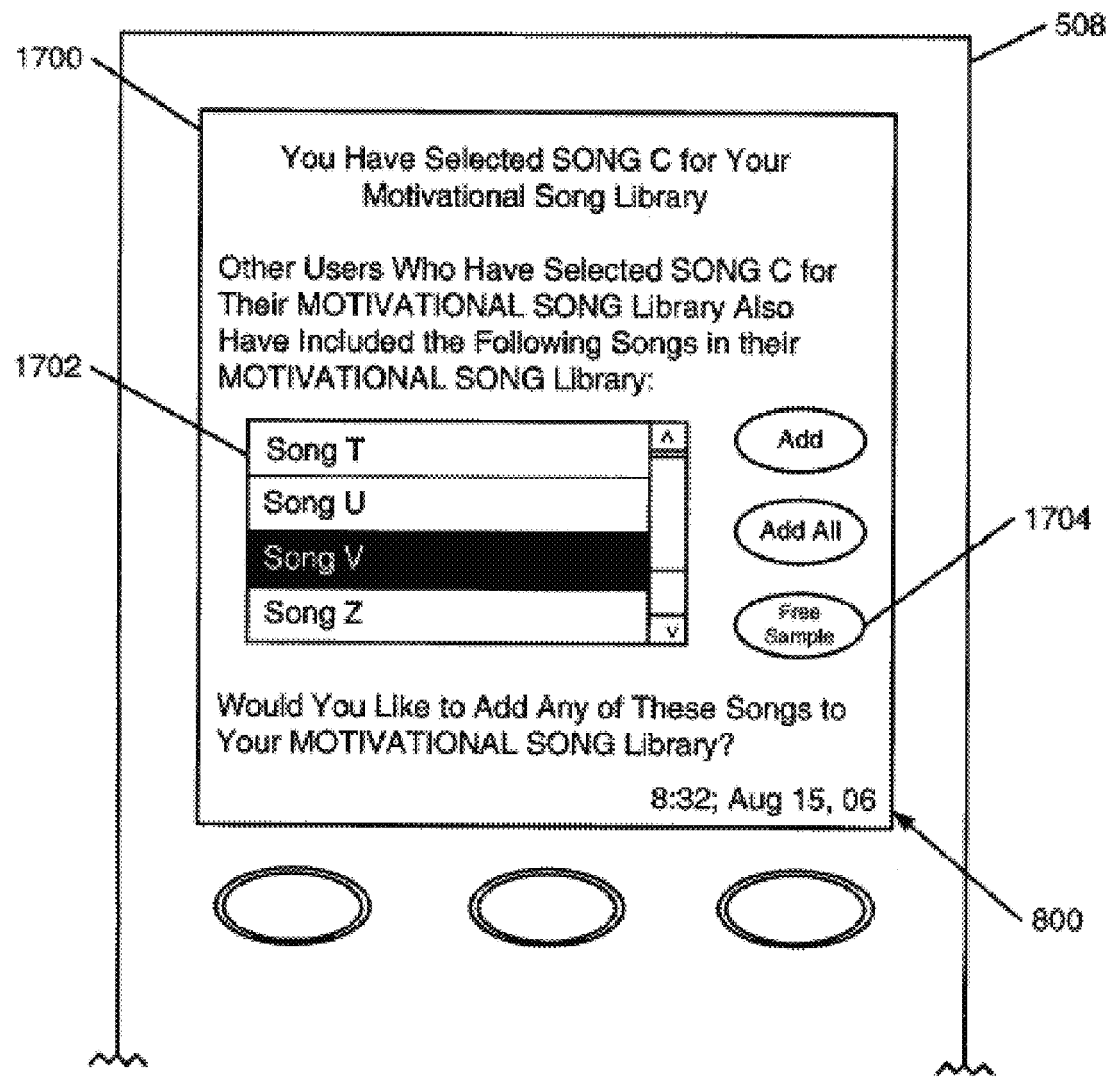

Systems and methods according to at least some examples of this invention may provide additional features relating to motivational songs and/or motivational song libraries. As described above, systems and methods according to at least some examples of this invention may connect to a remote system (e.g., system 704 from FIG. 7), for example, over the internet or another networked connection. Because the remote system also may receive data from other users, systems and methods according to examples of this invention may suggest or recommend media content to one user (e.g., motivational song content) based on motivational song information supplied by other users. For example, upon selection of a motivational song for one's motivation song library (as shown in FIG. 16), systems and methods according to at least some examples of this invention may provide suggestions or recommendations for additional motivational songs for the user's library. FIG. 17 illustrates one example of a user interface 1700 for performing this function. As shown in FIG. 17, upon selection of a specific song for the user's motivational song library, systems and methods according to this example of the invention may review the selection history of that song and/or the motivational song libraries of other users of the system (e.g., using remote system 704) and provide a listing 1702 of other suggested motivational songs based on the motivational song libraries of other users that have selected the same song for their motivational song library. Once the listing 1702 has been generated and presented to the user, the user may select one or more of the songs from the listing 1702 for inclusion in their own motivational song library. If necessary, appropriate interfaces may be provided to enable users to download and/or purchase any of the desired songs, e.g., from commercial and/or on-line sources. The "Free Sample" icon 1704 allows users to experience at least some portion(s) of a suggested song or media content, such as a movie clip (e.g., if they do not recognize the content), to provide additional information on which to base their selection decision.

Suggestions for additional songs (including motivational songs) or other media content are not limited to suggestions based on a specific song (or other content) selected by a user, and they are not limited to suggestions based on selections made by other users that have used the same song (or content). Based on the overall content of a user's song library, favorites listing, most played listing, motivational song library, etc., systems and methods according to at least some examples of this invention may suggest additional songs based on other factors, such as: songs from the same artist or groups as the songs included in one or more of the user's libraries or listings; songs of the same genre as the songs included in one or more of the user's libraries or listings; songs having the same or similar beat or cadence as the songs included in the user's libraries or listings; etc. Other similarity factors also may play a role in making these suggestions, such as similarities in age, gender, hobby listings, etc. Appropriate interfaces may be provided, e.g., like those described above in conjunction with FIG. 17, to display listings or titles of suggested songs to the user; to enable users to download and/or purchase any of the desired songs, e.g., from commercial and/or on-line sources, if necessary; to allow user "sampling;" etc.

Figure 18:
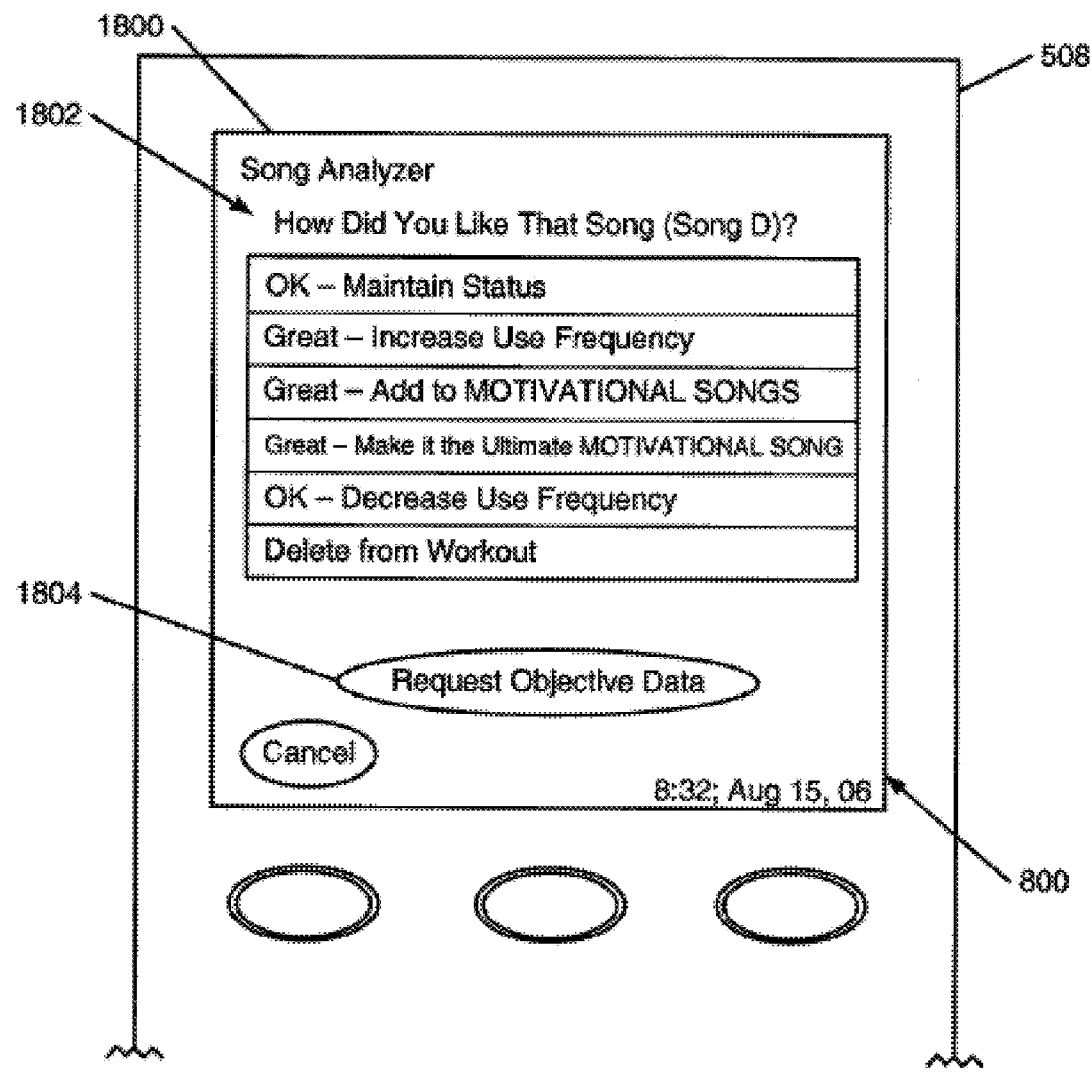

Subjective data, input by users, also may be used in systems and methods according to at least some examples of this invention, e.g., to at least in part control use and/or status of the media content (e.g., songs, videos, etc.). FIG. 18 illustrates one example. As a workout progresses and presentation of a song (or other media content) is completed, systems and methods according to at least some examples of this invention may request subjective user feedback relating to the song or other content. As shown in FIG. 18, the user interface 1800 of this example includes an area 1802 requesting that the user indicate how much they liked the previous content. In this illustrated example, the user may provide six potential responses to this inquiry, namely: (a)

maintain the song at its current status (e.g., in its current play lists, at the same play frequency, etc.); (b) increase its play frequency; (c) add to "motivational songs library" (e.g., a motivational song as described above); (d) make it the "ultimate motivational song" (e.g., the ultimate motivational song as described above); (e) decrease its play frequency; and (f) remove it from the workout. Of course, these are just examples of potential options that may be included in area 1802. If desired, without departing from this invention, additional options may be included, one or more of the listed options may be omitted, other ways of presenting the options may be provided, etc.

FIG. 18 illustrates another feature that may be made available in systems and methods according to at least some examples of this invention. As described above, systems and methods according to at least some examples of this invention may include an electronic module 502 and/or other devices for sensing, tracking, and/or storing characteristics of the user's athletic performance (e.g., a speed and/or distance monitoring system, a cadence detecting or monitoring system, a physical or physiological parameter measuring system, etc.). The objective data relating to the user's athletic performance may be tracked with respect to the music or other media content presented to the user via electronic device 508 during the workout. In this manner, the objective effect of the media content on the user's athletic performance (if any) may be tracked, and the user can make decisions about the status of specific media content (e.g., its inclusion in a play list, its play frequency, its status as a motivational song, its status as the ultimate motivational song, etc.) based, at least in part, on objective data correlating the presentation of the content and the user's actual performance. In other words, systems and methods according to at least some examples of this invention may be used to identify songs and/or other media content that positively or negatively affect the user's athletic performance, optionally with respect to different activity types (e.g., while running, while using an elliptical machine, during weight lifting, etc.).

As more specific examples, for at least some users, presenting content having a beat (e.g., music beat or tempo) that closely corresponds to or matches the user's cadence during the workout activity (e.g., step landing during running, cycling or elliptical training machine foot presses or push-offs, rowing pulls, etc., for example, two music beats per step or exertion, or the like) can positively affect the user's performance. In other words, some users may consciously or subconsciously try to keep their steps or other exertion cadence in time with the music beat. This action may help these users maintain an increased pace for a longer time period (i.e., they may try to maintain cadence in time with the music, even as they tire and would normally slow down). The opposite effect also is possible (e.g., users may slow their step or exertion pace or cadence when music content having a slower beat is presented). Accordingly, systems and methods according to at least some examples of this invention (e.g., systems and methods that can correlate user performance characteristics with audio/video content presentation) also can be used to identify music and other content for users that may enhance and/or has been demonstrated as enhancing their performance. Additionally, by using data relating to music or other content having a positive effect on user performance, systems and methods according to this example of the invention may identify other content having similar characteristics (e.g., similar genre, beat, etc.), and the systems and methods may automatically suggest or present this content (e.g., songs) to the user. As yet additional examples, if desired, systems and methods according to at least some examples of this invention may alter the playback characteristics of music or other content to better match the characteristics of content demonstrated as having positively impacted the user's performance (e.g., speed up and/or slow down the music beat or playback of the music or other content to better match the beat of other positively impacting content, to better match user cadence or step pace, and/or to help alter user cadence, etc.).

Figure 19:
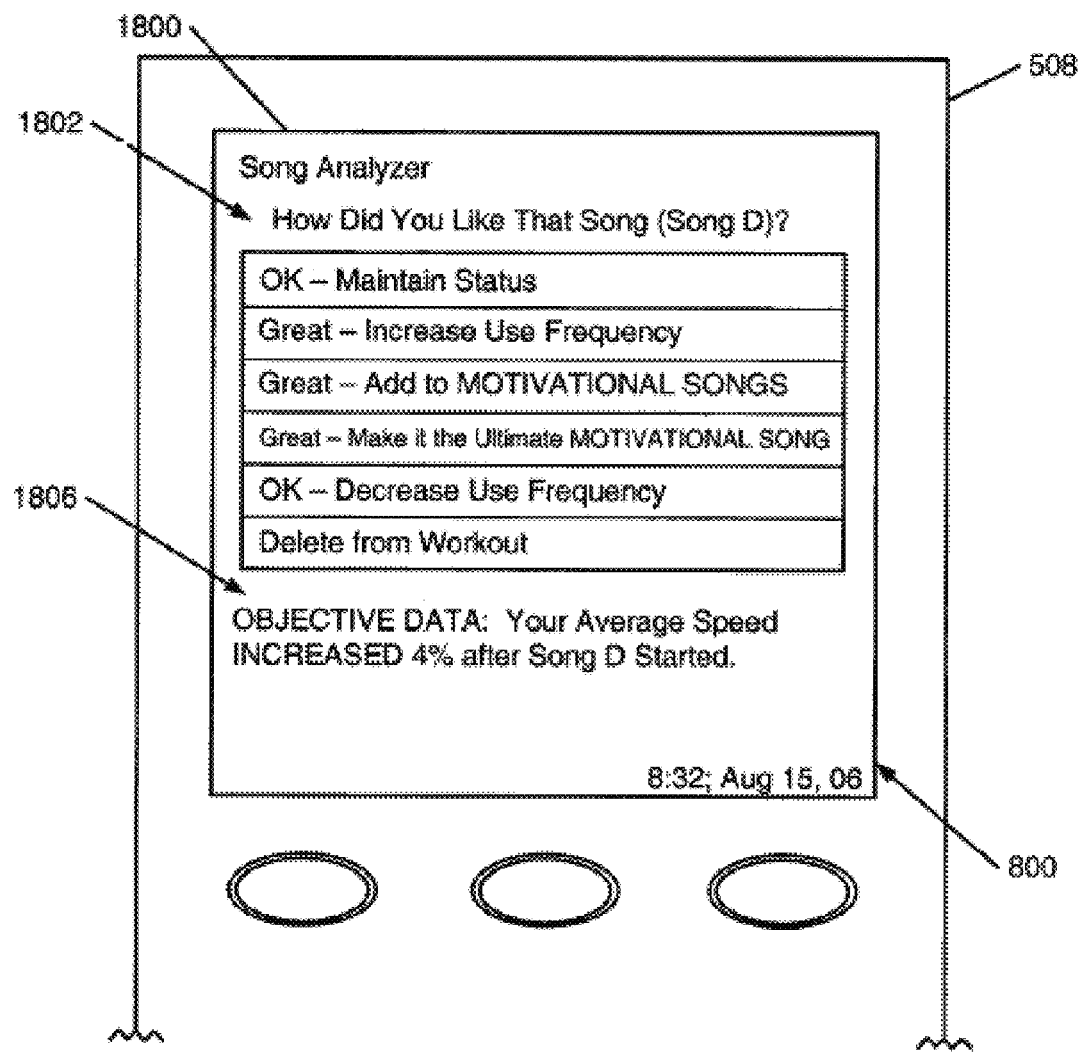

As shown in FIG. 18, the user interface 1800 includes an icon 1804 that allows users to request objective data relating to their performance during presentation of the identified song (or other media content). Selection of this icon 1804, in this illustrated example, changes the interface screen 1800, as shown in FIG. 19, to present objective data, if available, that relates to the user's athletic performance during presentation of the song (or other media content). In this illustrated example, area 1806 of the interface 1800 indicates performance change data (if any) that was sensed during presentation of the identified song (or other media content). If desired, the user can then make changes to the song's status, e.g., in area 1802, in the manner described above, based on this additional objective data. If desired, in at least some instances (e.g., when a strongly positive or negative performance impact is sensed), the objective data may be presented to the user automatically, without the need for user interaction or selection (e.g., using the interface 1800 and/or icon 1804, etc.).

Storing information relating to the objective impact of music or other media content on a user's athletic performance may be used in other ways by systems and methods according to at least some examples of this invention. For example, by identifying songs (or other media content) that appear to positively affect the user's performance, systems and methods according to at least some examples of this invention may be used to automatically present these songs at desired times during a workout (e.g., during an intense portion of a workout, when slowing is sensed, when predetermined goals or milestones are within reach, when a new personal best is within reach, etc.). In effect, using the objective performance data, systems and methods according to at least some examples of this invention can automatically generate a "motivational song library" and/or identify an "ultimate motivational song," as generally described above. Such automatically generated or identified content may be used in addition to and/or in place of the subjective and user identified libraries and/or content described above. Any desired conditions or parameters may be used in identifying a song or other media content for inclusion in the automatically generated "motivational song library" and/or "ultimate motivational song" (e.g., increased speed or other performance parameter by 1%, 2%, 3%, or more, etc.).

In addition to use of the objective data as correlated with media content output to provide an automatically generated "motivational song library" and/or "ultimate motivational song," the objective data may be used by systems and methods according to at least some examples of this invention, at least in part, to create entire workout routines for the user (including mixed music). For example, the objective data may be used to create workout routines including one or more activity types wherein music and/or other content is selected automatically for inclusion and presentation during the workout routines (e.g., in an effort to enhance the user's performance) based on the objective data indicating songs or other content that has positively impacted the user's performance (optionally on an activity type by activity type basis) in the past.

In addition to using objective data from one specific individual for inclusion in a proposed workout routine for that individual, objective data relating to certain media content and its effect on performance may be shared with others, for example, via the remote source 704, over the network (such as the internet), etc. As some more specific examples, workout routines or portions thereof from one user (including the media content) may be used by systems and methods according to the invention to create workout routines or portions thereof for one or more other users (including the media content) and/or to present certain media content (found to positively impact the performance of at least one user) to one or more other users at certain times. Optionally, systems and methods according to examples of the invention also may use the objective data and media content, at least in part, to present a workout routine (including media content) from one user to users having one or more of the same general characteristics as the user, such as similar height, weight, fitness level, workout lengths, activity types, combinations of activity types, the same gender, same hobbies, etc.

VII. Miscellaneous Potential Features of Systems and Methods According to Examples of this Invention A wide variety of variations on the above-described features of systems, methods, and user interfaces therefor may be provided without departing from this invention, including variations on the user interface to include features commonly known and used in the art, e.g., features of commercially available computer and/or electronic device operating systems. While the following section describes certain potential and specific variations on features of systems, methods, and user interfaces therefor, those skilled in the art will recognize that other variations on these features and/or use or inclusion of other features are possible without departing from this invention. The following description of these specific features should not be construed as limiting or requiring systems, methods, and user interfaces according to the invention to include these specific features and/or as indicating that systems, methods, and user interfaces in accordance with this invention may not include additional or different features.

VIII. Reward Programs and/or Enhanced Feature Sets for Certain Users

Systems and methods according to at least some examples of this invention are not limited to situations and/or arrangements in which an electronic module (e.g., module 502, a pedometer type speed and/or distance measuring electronic module, a physical and/or physiological parameter measuring module, etc.) is included as part of or mounted in a receptacle provided in an article of footwear. Rather, the electronic module may be included in a variety of different products, such as in apparel (e.g., a shirt or jersey, as shown in FIG. 1); provided as a separate element carried or worn by the user; attached to the user's body, clothing, shoes, equipment, etc. (such as the wrist band element or the adhesively applied module shown in FIG. 1); etc. Any desired manner of mounting or carrying the electronic module may be used in accordance with at least some examples of this invention.

Even for modules that may be mounted and effectively used at various different locations or positions on a user's body or the like, systems and methods according to at least some examples of this invention may provide different functionality to the module and/or the overall athletic performance sensing and/or tracking system based on the manner in which the module is mounted, the equipment to which it is mounted, the manner in which it is used, the items or arrangement with which it was purchased or obtained, etc. As examples, if desired, users of systems and methods according to at least some examples of this invention may receive various "rewards" and/or "enhanced feature sets" when the modules are purchased and/or used with equipment provided by a certain manufacturer (e.g., purchased, mounted, and/or used in a predetermined manufacturer's clothing, footwear, and/or other equipment, etc.).

Any desired way of providing and/or activating the "reward" and/or "enhanced feature set" may be provided without departing from this invention. For example, the clothing, footwear, and/or other equipment for use with the module may include at least some portion of an activation and/or authentication system that interacts with the electronic module in some manner to provide and/or trigger availability of the "reward" and/or "enhanced feature set." Examples of such activation and/or authentication systems are described, for example, in U.S. patent application Ser. No. 11/166,351 filed Jun. 27, 2005, U.S. patent application Ser. No. 11/407,328 filed Apr. 20, 2006, and U.S. patent application Ser. No. 11/416,458 filed May 3, 2006. Each of these patent applications is entirely incorporated herein by reference. As another example, if desired, when a user purchases a module "enabled" or "ready" article of clothing, article of footwear, and/or piece of athletic equipment, they may be given coupons, an internet code, password, other access code, or other information that directly provide, activate, and/or provide access to the "reward" or "enhanced feature set." Other ways of activating and/or obtaining a "reward" and/or "enhanced feature set" and/or authenticating use of the electronic module with a particular article of clothing, article of footwear, and/or piece of athletic equipment may be used without departing from this invention.

The "reward" and/or "enhanced feature set" also may take on any desired form without departing from this invention. For example, as noted above, the "reward" may constitute a coupon (paper or electronic) for free or discounted merchandise (e.g., discount off future purchases, discount on the electronic module (or other equipment) when purchased with footwear, clothing, or equipment from a participating manufacturer, etc.); rebate offers; free additional merchandise with purchase of the module and footwear, clothing, or equipment from a participating manufacturer; etc. As additional examples, if desired, the remote system (e.g., system 704 in FIG. 7, such as a website, server, etc.) or other system for receiving, storing, processing, and/or managing the athletic performance data (e.g., run on or through computer 702 in FIG. 7) may provide enhanced functionality for module users who also have purchased footwear, clothing, or equipment from a participating manufacturer (e.g., longer term storage of data, additional interface features, additional data processing and/or display features, etc.). As yet further examples, if desired, the "reward" or "enhanced feature set" may constitute free access to a website or other computer program (optionally a limited time free access or introductory period) for storing and processing the athletic performance data for module users who also have purchased footwear, clothing, or equipment from a participating manufacturer (while module users who have not purchased footwear, clothing, or equipment from a participating manufacturer would be required to pay a fee or a higher fee for access to the website or computer program, optionally a monthly or other subscription type fee, etc.). A wide variety of other types of "rewards" and/or "enhanced feature sets" are possible without departing from this invention.

IX. Athletic Performance Data Presentation

As is known, conventional athletic performance and exercise equipment is capable of presenting data and information to users regarding their performances or workouts (e.g., distance, time, speed, calories burned, metabolic equivalents ("METs"), etc.). Systems and methods according to at least some examples of this invention may be programmed and adapted to provide performance data and/or information to users in other forms or formats, e.g., so as to be more entertaining, motivational, goal-oriented, etc. For example, as for distance, rather than merely indicating miles or kilometers traveled, the distance data (e.g., distance traveled for a given workout, distance traveled over the course of two or more workouts, total distance traveled, etc.) may be presented as an indication of the distance traveled in the "real world." As more specific examples, the distance traveled data may be presented as a map of a relevant area (e.g., a user's local area, a state map, a U.S. map, a world map, etc.) showing the distance traveled by the user on the map. Such a presentation tool can help provide motivation and/or help users better define and visualize goals. For example, a user may have a "goal" of running on a treadmill or riding a stationary bicycle a distance "across their home state" within a specific time period (e.g., a month) or "across the U.S." within a specific time period (e.g., a year). Presenting such user's progress on a map can help them easily visualize their goals and current progress and/or provide motivation to continue working toward the goal in the future. Multiple users, optionally users involved in a virtual race, competing with one another, and/or striving to achieve a common goal, may be shown on a single map, e.g., for further motivational purposes.

The user's progress and/or goal may be presented on a map of any desired area without departing from this invention (e.g., a locally relevant map, a map of an area familiar to and/or selected by the user, etc.). Additionally or alternatively, the map may be changed over time, optionally automatically by systems and/or methods according to this invention. For example, for users with long distance running or biking goals, the displayed map may change as certain milestones are approached and/or achieved. For example, progress for a treadmill or exercise bicycle user having a goal of running or biking "across the U.S." may be displayed in various ways as the user's distance accumulates over time. During a workout in which the user's accumulated distance passes or approaches 350 miles, systems and methods according to at least some examples of this invention may display a map including San Diego, Calif. and Phoenix, Ariz. and advise the user, for example, as follows: "Congratulations. Today you passed the 350 mile mark toward your goal. As shown in this map, had you begun running in San Diego, you would have reached Phoenix today!" At a later time, this same user may reach the 700 mile mark. On that day, systems and methods according to this example of the invention may display a map including Washington, D.C. and Chicago, Ill. and advise the user, for example, as follows: "Congratulations. Today you passed the 700 mile mark toward your goal. As shown in this map, this is equivalent to the distance between Washington D.C. and Chicago, Ill. Keep up the good work!" Of course, a wide variety of messages, maps, starting/ending locations, and the like may be used without departing from this invention, and user input may be provided, at least in part, to indicate or define these features.

"Real world" goals for other workout activity types may include, for example: a total weight lifted goal (e.g., pounds.times.# of sets.times.# of repetitions/set, etc.) sufficient to lift the Brooklyn Bridge; total number of floors or hill incline climbed goal sufficient to climb Mt. Everest; total number of miles rowed goal sufficient to row across Lake Michigan; total miles skied goal sufficient to ski to the North Pole; etc. Any desired "real world" goals may be presented visually or in other manners in an effort to entertain and motivate users and to keep them interested in continuing their workout routines over time.

Other measured workout parameters also may be usefully expressed in "real world" terms, e.g., for entertainment, motivational, and/or goal-driven purposes. As further examples, information relating to workout intensity data (e.g., such as calories burned, METs, etc.) may be presented or displayed in more "real world" forms or formats. As more specific examples, "calorie" data and information may be presented (e.g., before a workout as a goal, during a workout, and/or in a post-workout analysis) in real world terms as being equivalent to certain foods or beverages. Of course, the display may present any desired food or beverages to the user without departing from this invention. As examples, if a user selects a "calorie burn" goal before beginning a workout, systems and methods according to examples of this invention may display icons or pictures of food or drink corresponding to the calorie burn goal (e.g., three hamburgers, two glasses of wine, a complete meal, etc., displayed, for example, on the exercise equipment display, on the portable electronic device 508, etc.). Then, as the workout progresses, these icons or pictures could disappear and/or change in appearance to indicate the extent to which the workout has been completed. Any desired way of presenting and/or changing the pictures or icons may be used without departing from this invention, such as: changing the color of the icon or picture (optionally in portions as the workout progresses); causing an increasing portion of the icon or picture to fade, gray, or disappear, etc.; causing an increasing portion of the icon or picture to colorize or appear; "X"-ing out the icon or picture (e.g., slowly superimposing an "X," "No" symbol, or similar character or icon over the food or drink icon or picture, etc.); etc. Additionally or alternatively, calorie burn data and information after the workout (or at other times) may be displayed (e.g., on the exercise equipment, on the electronic device 508, on a post-workout analysis computer (such as computer 702 in FIG. 7), etc.) as the equivalent food, drink, and/or meal pictures or icons.

X. Special or Targeted Workout Goals

As described above, systems and methods according to at least some examples of this invention may be used to provide pre-programmed workouts for users (optionally, user designed workout routines, third party designed workout routines, purchased workouts, downloaded workouts, combinations thereof, etc.). Such workouts may include a variety of different activity types, and optionally activities that change from workout-to-workout (e.g., different types of activities on different days, different workout parameters on different days, etc.).

Systems and methods according to some examples of this invention, may allow users to define their workouts and/or goals in other ways as well. For example, users may state their goals in more "real world" terms, such as: a "pre-wedding" (or pre-prom, pre-class reunion, or other event) weight loss workout program; a "swimsuit" workout program; a "flabby arm management" workout program; a "blood-pressure reduction" workout program; a "cholesterol control" workout program; etc. Given these "real world goals," optionally in combination with other data relating to the user or the goal (e.g., gender, height, weight, current fitness level, workout history, date of event, etc.), systems and methods according to at least some examples of this invention may provide a workout program designed to help the user better achieve the desired goal (optionally, receiving input from professionals).

The workout programs may be designed by third parties (e.g., coach, nutritionist, trainer, physician, etc.), optionally specially designed for the specific requesting individual, or they may be automatically selected by systems and methods according to the invention from previously designed and stored workout programs available to users. The workout routine for any individual day may be downloaded, for example, from another source (e.g., remote computer 704 or local computer 702 in FIG. 7, from a disk or other memory device, etc.) to the electronic device 508, electronic module 502, interface device 506, etc., which optionally may be used to control exercise equipment and/or other aspects of the workout, as described above.

XI. Other Data or Information Presentation Techniques

User movement or activity when working out or participating in an athletic event or performance may make it difficult, in at least some instances (e.g., during particularly intensive portions of the workout or event, etc.), to read detailed information provided on a screen 800 of a small electronic device 508 (e.g., particularly if the information is presented in small fonts, etc.). Systems and methods according to at least some example embodiments may be designed to provide at least some information to users in a quickly identifiable manner, e.g., in a manner that will not require reading small print.

One way of providing information to users in a quickly identifiable manner relates to the background color present on the display screen 800. For example, if desired, systems and methods according to at least some examples of this invention may make certain background colors correspond to a physical or physiological parameter associated with the workout. As more specific examples, the background color may be correlated to physical or physiological parameters such as current heart rate, total calories burned, total distance traveled, current pace, percentage of workout completed, etc. While any desired correlation between the background color and the physical or physiological parameter may be used without departing from this invention, in some examples of this invention the color may change over the visible spectrum (e.g., purple (for light/resting/beginning physical or physiological parameters, such as resting heart rate) changing to red (for heavy/intense/ending physical or physiological parameters, such as heart rate approaching a dangerous or desired maximum level), optionally with intermediate changes through one or more of blue, green, yellow, orange, etc. to indicate intermediate levels for the physical or physiological parameter(s). Of course, any numbers of colors, color combinations, color change schemes, and the like (including gray-scaling, cross-hatching or shading, line or font types/characteristics, etc.) may be used without departing from this invention. The color coding key (e.g., which colors are used and the manner in which they correlate to the levels of the physical or physiological parameters) may be user selected; pre-set by the system and/or method; determined based, at least part, on the user's personal characteristics (e.g., age, gender, height, weight, fitness level, history, etc.); and/or set in any other desired manner and/or using any other desired information.

The entire background of the screen 800 need not be changed or color coded to take advantage of these example aspects of the invention. As another example, if desired, a border of the screen 800 may include these types of color change and/or color coding features (more than one border may be provided or more than one color coded parameter may be provided using a single (potentially multi-colored) border, if desired, to provide information for more than one parameter). As another example, a portion of the screen (e.g., an "intensity block" in the upper left corner, etc.) may be provided to include one or more of these types of color change and/or color coding features. As yet additional examples, the desired physical or physiological data may be presented graphically or pictorially, such as by a bar graph, a "progress" chart (e.g., like those used to show download time remaining in commercially available computer operating systems), an analog type display (e.g., an analog speedometer or tachometer type display, etc.), a bouncing ball or other icon element (e.g., similar to graphic elements provided in conventional sound equalizer devices and/or applications), etc. As yet another example, font color (rather than background color) may be changed (e.g., using the color schemes described above) to quickly and easily provide information to users, e.g., of the types described above.

XII. Fitness/Workout/Intensity Indices

Systems and methods according to at least some examples of this invention may allow users, equipment manufacturers, coaches, trainers, or others to design their own parameters or indices for tracking one's fitness, workout difficulty, workout intensity, and/or other workout characteristics. Any desired data and/or information may be used to formulate these indices, such as: age; gender; height; weight; workout intensity data (e.g., speed, set resistance levels, set incline levels, number of sets, number of repetitions, etc.); workout time/duration; elapsed time; elapsed distance; user's workout history; calorie burn; METs; etc. Any desired mathematical formula, algorithm, or scheme for combining information relating to one or more of these data items may be used without departing from this invention to arrive at a desired "index" to measure, track, and/or compare the fitness and/or workout characteristics of one or more individuals.

XIII. Auto-Pause of Media Content Playback

The systems and methods described herein may include one or more processes for automatically pausing playback of music and/or other forms of digital media content, including, among others, videos, podcasts, navigational instructions from a navigational device, live radio broadcasts, live television broadcasts, and combinations thereof. Furthermore, audio (music), and video data may be stored locally in memory, such as memory 212, or remotely, on one or more servers or equivalent storage devices. Furthermore, audio and/or video data may be stored in files using any known file/compression format, such as, among others, .mp3, .AVI, .MP4, and the like. In this regard, although certain media content may be streamed or transmitted in packet-switched networks, those skilled in the art will appreciate that a plurality of packets transmitted at different times may constitute a single "file" or piece of media content. As such, in the disclosure that follows, where reference is made to one or more processes for automatic pausing of music playback, those of ordinary skill in the art will recognize that substantially similar systems and methods may be used in conjunction with other forms of digital media content, without departing from the scope of this disclosure. For example, in accordance with other embodiments, one or more systems and methods may be applied to mute and/or lower a volume of playback of an audio component of digital media content and/or transition away from a visible video component of the digital media content, with/without pausing playback.

Other examples may include interrupting or disabling wireless radios or interfaces. With reference to pausing, it can be discerned from other actions, such that transmission or playback of the media content is ceased or interrupted at specific location of the content so as to not be presented (e.g., audible or viewable) to the user, however, upon resuming playback, the content will be resumed at a specific location—such as the first location. In other embodiments, it may be resumed at a second location, which may be prior to the first location (e.g., a few seconds prior to being interrupted or at a specific section break). In this regard, pausing is distinct from muting or otherwise "blocking" transmission of media being played. However, both instances are encompassed by various implementations of this disclosure. Thus, where reference is made to automatic pausing of playback of digital media content, those of ordinary skill in the art will appreciate that thus discussion is equally applicable to describe and enable other implementations, such as blocking transmission of media content being played.

In one configuration, the systems and methods described herein for pausing playback of media content may include one or more components and/or interfaces described in relation to FIGS. 6-19, wherein media content playback may be facilitated by device 508, and one or more interfaces may be similar to those displayed on interface screen 800. Accordingly, the systems and methods described in relation to FIGS. 20-28 may be implemented in conjunction with, among others, those embodiments configured for playback of motivational songs (FIGS. 16-19), and the like.

In one example, one or more processes are disclosed for automatically pausing playback of music content for convenience of a user of an electronic device, such as device 112, 114, 126, 128, 130, 400, and/or 508, as previously described. As such, the systems and methods described herein may execute one or more processes for auto-pausing of music playback for convenience of the user. In another example, the systems and methods described herein may execute one or more auto-pausing processes for a user's personal safety. Accordingly, FIGS. 20-28 illustrate example processes that may be executed to automatically pause playback of media content from one or more user devices. Furthermore, those exemplary processes of FIG. 20-28 may be executed by a device during an athletic activity. For example, one or more processes are disclosed for automatic pausing of media playback when a user is running. However, those of ordinary skill in the art will recognize that these disclosures may be applied to additional or alternative activities including, among others, walking, cycling, swimming, playing team sports, and the like. Furthermore, one or more of the processes described herein may be executed when a user is resting (standing/sitting down/lying etc.).

In another example, automatic pausing of content playback from an electronic device, such as device 112, 114, 126, 128, 130, 400 and/or 508, may be as a result of data (a data stream and/or individual data points) received from one or more sensors. As such, the systems and methods described herein for automatic pausing of music playback may be executed using sensor data received from one or more sensors including, among others, an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof. Furthermore, those of ordinary skill in the art will recognize that the one or more processes described in FIGS. 20-28 may be combined in any manner/order/sequence, such that automatic pausing of media content playback may be based upon received data from one or more sensor types, and the like.

In one configuration, a user may be presented with an option to select automatic pausing of music playback from a settings menu of a device, such as device 508. Accordingly, a display screen, such as display screen 800 of device 508, may be utilized to present one or more selectable settings to the user, and wherein automatic pausing of media content playback may be one of a plurality of settings presented to the user.

In one example, a device, which may be configured to be worn by a user during an athletic activity, such as device 112, 114, 126, 128, 130, 400 and/or 508, may have the capability to playback audio and/or video media content. For example, a device worn by a user during an athletic activity may include, among others, a mobile phone, portable media player, a fitness monitoring device, or a specialized device worn as a headset, wherein said devices have the capability of communicating an audio and/or video signal to the user. In one embodiment, a device may have a media content interface for communicating media content of the user, wherein the media content interface may be, among others, a headphone jack, a video screen, a Bluetooth interface, an IR transceiver, or a radio transceiver, or combinations thereof. In another implementation, media content playback may be facilitated by a playback mechanism, wherein a playback mechanism may include a processor, and may additionally include associated firmware and software, for transducing/de-coding/converting media content data into a form for playback to a user. This mechanism may, in one example, convert stored data (stored on a hard disk drive, solid state drive, disk media such as DVD, CD, among others) into data that can be communicated to a user as audio, video, and/or text information, and the like. Furthermore, a playback mechanism may comprise those elements for establishing compatibility with a Codec or a container format (examples of which include, but are not limited to: .AVI, Ogg, DivX, MPEG etc.)

In one example, a user may listen to music through one or more headphones and/or speakers, wherein various styles and/or configurations of headphones and/or speakers will be readily apparent to those of ordinary skill in the art, including wired and wireless headphones and/or speakers, and the like. As such, in one example, a user's ability to hear sound from his/her surroundings may be partially or wholly impeded by music playback while wearing headphones/ listening using speakers. In this way, it may be advantageous to automatically pause playback of music (or other media content) during a specific time periods.

Figure 20:
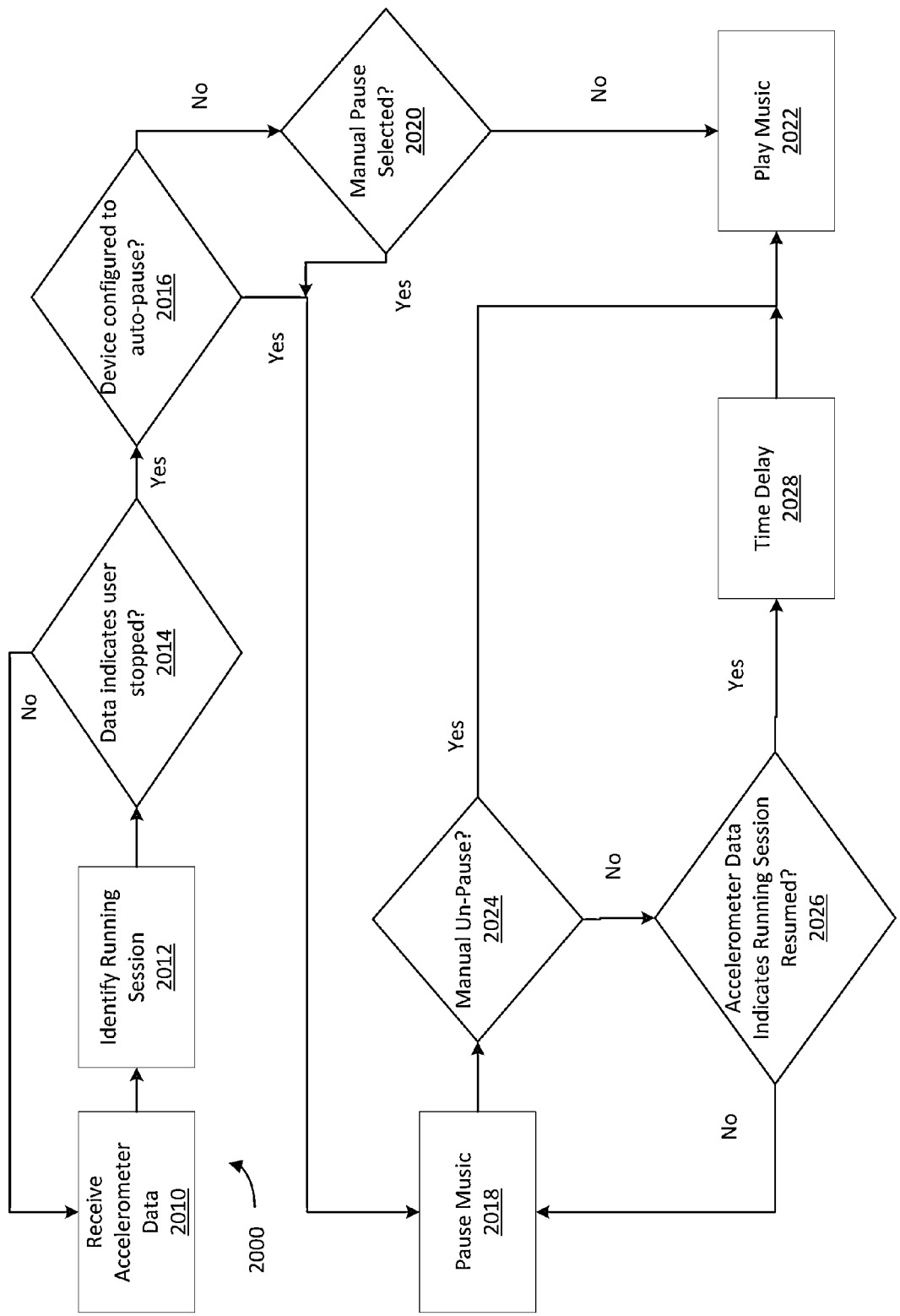
FIG. 20 is a flowchart diagram illustrating one or more processes for automatically pausing playback of media content to the user based upon received accelerometer data.

FIG. 20 illustrates a flow chart diagram 2000 for automatically pausing playback of music based on received accelerometer data. As such, FIG. 20 may be executed by one or more devices (112, 114, 126, 128, 130, 400 and/or 508) associated with and/or worn by a user. In one example, block 2010 may represent one or more processes for receiving accelerometer data from an accelerometer sensor associated with the device. In one example, sensor data may be received and processed by the processor, such as processor 202 from FIG. 2. Following from block 2010, block 2012 may execute one or more processes to identify a running session from the received accelerometer data. Accordingly, block 2012 may compare received accelerometer data to one or more models stored in the device worn by the user. In another example, however, received accelerometer data may be transmitted from a first device worn by the user to a second device, wherein said second device may or may not be worn by the user. In one example, the second device may process the received data, and subsequently transmit one or more results to the first device. In one example, a running session may be identified as a period of time during which the received accelerometer data indicates that the user is running. Furthermore, one or more processes for identifying activities, activity/athletic training sessions, and in particular, running sessions, and/or other activities comprising motion by the user may be identified. Accordingly, in one example, a user may listen to music during an athletic activity, wherein said music may be stored in memory on a device, such as memory 212.

As one example, upon identification of a running session, flowchart 2000 may proceed to block 2014. Block 2014 represents a feedback loop for analysis of subsequent data, such as for example, accelerometer data. In one example, block 2014 may execute one or more processes for identification of accelerometer data indicative of the user having stopped running (otherwise referred to as a "stoppage" and/or a "break"). In one example, received accelerometer data from the device may indicate that the user has stopped, or started to walk instead of run. In one instance, flowchart 2000 may proceed to block 2016.

Block 2016 represents one or more processes for checking that the user device is configured to automatically pause playback of content, such as music. Accordingly, if the user device is configured for automatic pausing of music playback, flowchart 2000 may proceed to block 2018, whereby one or more processes are executed to pause playback of playing music. Conversely, if the user devices not configured for automatic pausing of music playback, flowchart 2000 may proceed to decision 2020. In one embodiment, a user interface may prompt the user whether they wish to pause the media. For example, instead of automatically initiating the pause, an implementation may automatically issue a prompt or query to the user seeking a user input as to whether the media should be paused.

In one example, a user may manually pause music playback, as indicated at decision 2020. If, however, the user does not select to manually pause music playback at decision 2020, flowchart 2000 may proceed to block 2022, wherein playback of the music is continued.

Decision 2024 represents one or more processes to check as to whether a user has manually un-paused (resumed) music playback. If, at decision 2024, an indication is received that the user has manually un-paused music playback, the flowchart proceeds to block 2022, wherein playback of the music is resumed. If, however, a user does not manually un-pause music playback at decision 2024, flowchart 2000 proceeds to decision 2026. Accordingly, manual input by the user for pausing/un-pausing playback, among others, may be facilitated by one or more interface controls displayed to a user/configured as part of the hardware of a device, such as device 508 from FIGS. 6-19. In one configuration, a user may interact with on-screen controls for pausing, un-pausing, fast-forwarding, and/or rewinding using a display screen 800 which comprises a capacitive touch-screen.

Decision 2026 represents one or more processes for analyzing received data for one or more indications that a user has resumed a running session. Accordingly, the one or more processes executed at decision 2026 may be substantially similar to those executed at block 2012, and the like. In response, if it is determined that the user has not resumed a running session, flowchart proceeds from decision 2026 to block 2018, wherein music playback remains paused. If, however, it is determined, at decision 2026, that the user has resumed a running session, flowchart 2000 proceeds to block 2028. In one embodiment, block 2028 represents one or more processes to delay resumption of music playback by a predetermined time delay amount. In one example, a predetermined time delay may be one second, two seconds, five seconds, 10 seconds, among others. It will be readily apparent to those of ordinary skill in the art that any time delay amount may be used herein without departing from the scope of this disclosure, and those of ordinary skill in the art will be able to envisage various different implications for executing a time delay, such as that described. For example, one or more sensor values may determine a time delay. Accordingly, upon elapse of a predetermined time delay, flowchart 2000 proceeds to block 2022, wherein playback of the music is resumed.

In some embodiments, blocks 212, 2014 and/or decision 2026 may be implemented by a hardware or software module, which may be referred to as a "training session module", and blocks 2018 and/or 2022 may be implemented by a hardware or software module which may be referred to as a "playback module".

Figure 21:
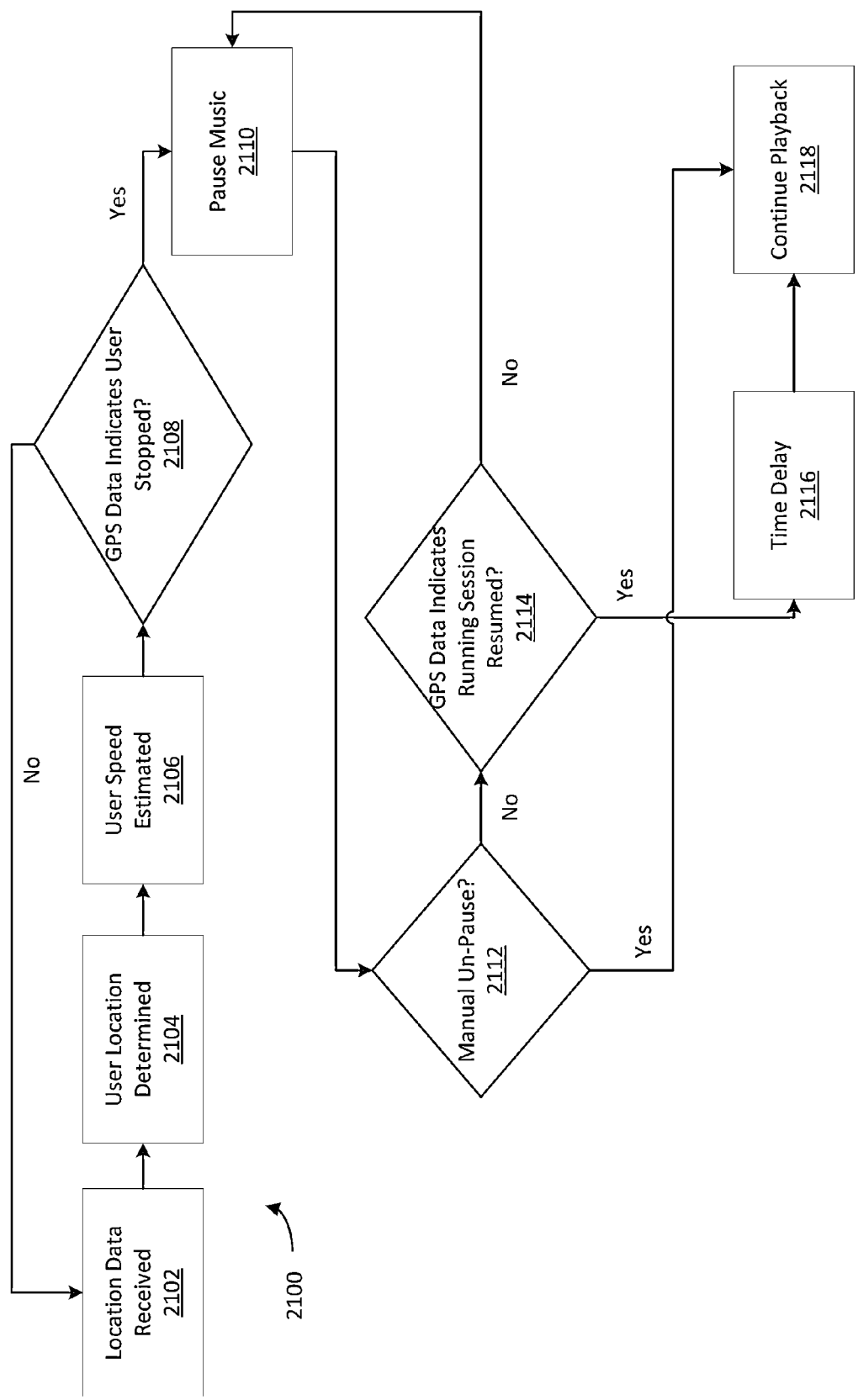
FIG. 21 is a flowchart diagram illustrating one or more processes for pausing playback of media content of the user based upon GPS data.

FIG. 21 illustrates a flowchart diagram including one or more processes for automatically pausing playback of media content based upon received location data (e.g., GPS and/or triangulation data). In one example, flowchart 2100 commences at block 2102 with the receipt of one or more data points from a GPS sensor, wherein said GPS sensor may be associated with a device, such as device 112, 114, 126, 128, 130, 400 and/or 508, worn by a user. Block 2104 of flowchart 2100 may execute one or more processes for determining a geographic location of the user based upon received GPS data, wherein those of ordinary skill in the art will recognize various processes for determination of a geographic location based on GPS data. In one example, block 2106 represents one or more processes to infer/calculate an estimated speed of the user from determined location data. For example, the rate at which a user's location is changing may be used to determine a speed at which a user is traveling, and the like. In one example, one or more processes executed at block 2106 may determine whether a user is running or walking and/or conducting any other motions, wherein said information may be used to identify an activity session being carried out by a user.

Decision 2108 of flowchart 2100 represents one or more processes to identify that a user has stopped moving during an activity session. For example, block 2108 may represent one or more processes to identify that a user has stopped performing a certain action and/or activity. For example, it may be determined that a user stopped running during a running session, among others. Upon identification of the stoppage, flowchart 2100 may proceed to block 2110, wherein block 2110 represents one or more processes to pause playback of media content, such as music, and the like. Looking to decision 2112, a user may manually un-pause (resume) playback of music, wherein playback is continued at block 2118. If, however, a user chooses not to manually un-pause music playback, flowchart 2100 proceeds to block 2114, wherein subsequent data (e.g., GPS data) is analyzed to determine whether the user has resumed running Upon determining that a user has resumed running, the flowchart proceeds to block 2116, wherein block 2116 may represent one or more processes to delay playback of paused music. In one example, a time delay may be similar to time delay 2128 from FIG. 20, wherein said time delay may be used to ensure that the user has resumed running.

Figure 22:
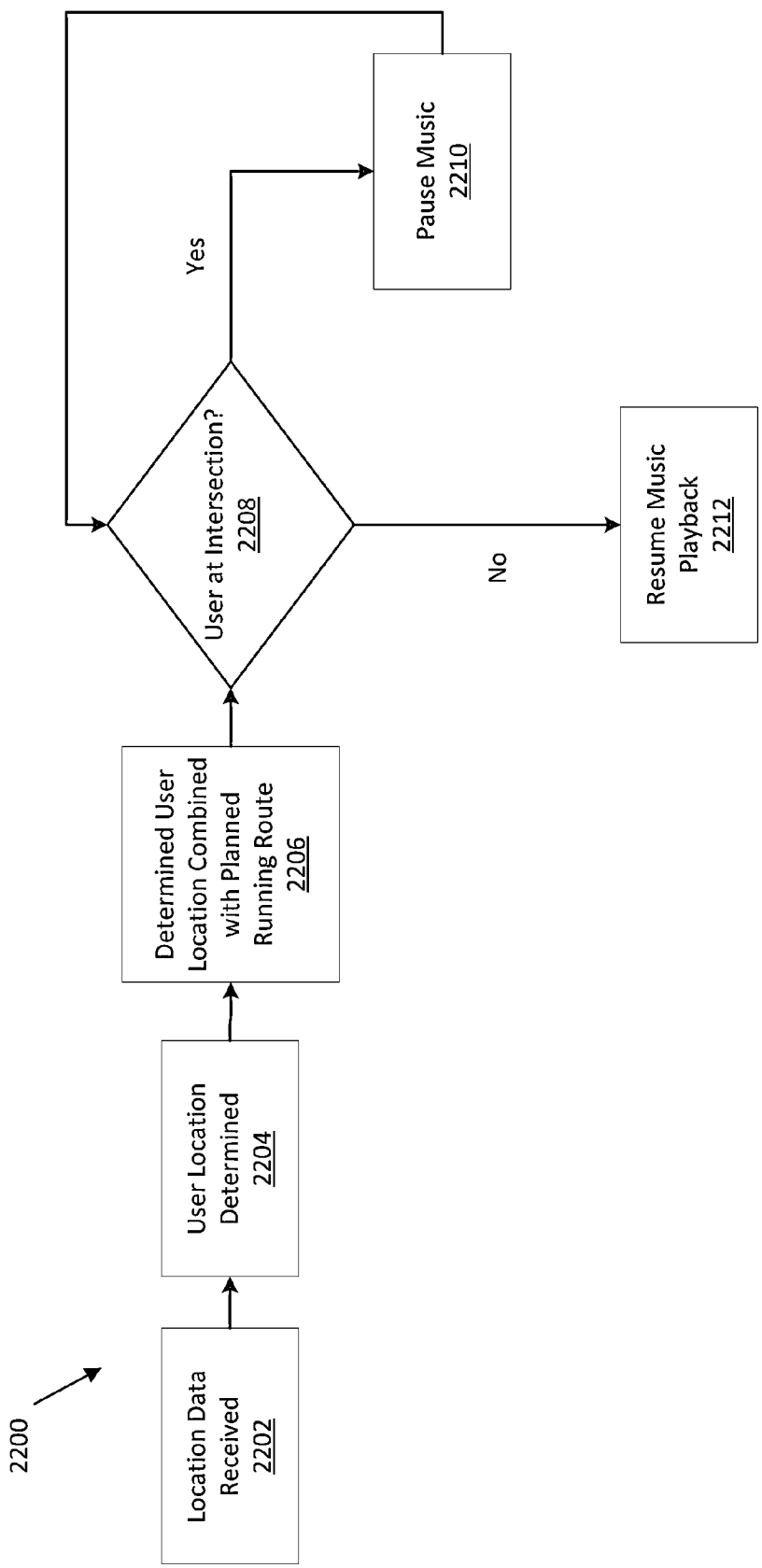
FIG. 22 illustrates another flowchart including one or more processes for pausing playback of media content of the user based upon received GPS data.

FIG. 22 illustrates a flowchart diagram including one or more processes for automatically pausing playback of music based upon received location data (e.g., GPS data). In one example, and at block 2202, one or more data points may be received from a GPS sensor. In a similar manner to that described in relation to block 2104 from FIG. 21, block 2204 may execute one or more processes to determine a geographic location of a user from received GPS data. In one example, a user may, before starting a training session, plan a running route using a mapping tool/program that is separate to the device worn by the user, or is integrated into the device worn by the user, and the like. As such, information related to a planned running route of the user may be made available to a device worn by the user during an athletic activity. The running route may be stored in a hardware and/or software module known as a "route storage module". Furthermore, at block 2206, one or more processes may be executed to combine planned route information with determined user geographic location information. In one example, one or more processes may identify one or more intersections, such as on a planned route, and/or within a predetermined distance of a user's current geographic location. As used herein, an intersection encompasses two or more different paths that intersect, including a road, railroad, bike path, sidewalk, running path, and/or combinations thereof in proximity to the user. For example, a road may intersect with a railroad crossing. In one embodiment, an intersection may be detected up ahead of the user (e.g., in the general direction of the user's travel and/or in accordance with a planned or estimated route). In response, certain embodiments may pause (or stop) playback of media content until the user has traveled through the road intersection. In certain embodiments, it may be determined that the user is at least a first distance past the intersection. In other embodiments, a time delay may be utilized, including variations of time delay based on the type of intersection.

Accordingly, in one example, flowchart 2200 may include one or more processes for automatically pausing playback of music upon a determination that the user is approaching an intersection. In this way, flowchart 2200 may be utilized for allowing a user to be more alert to one or more sounds of road traffic when crossing at an intersection during an athletic training session, which may be a running session or a walking session, among others.

Decision 2208 represents one or more processes that may identify the user's current geographic location relative to one or more identified intersections. If it is determined that a user is currently positioned at, or within a predetermined distance of, an intersection (which may be part of a planned route), flowchart 2200 may proceed to block 2210, wherein music playback to a user may be automatically paused (or the user may be presented with option to pause the media). In one example, a predetermined distance from an intersection may be, among others, 5 m, 10 m, 15 m, or 20 m, or any predetermined distance, and represented using any unit of length. Correspondingly, upon determination that a user's current location is outside of a predetermined range of a intersection and/or time delay, flowchart 2200 may proceed to block 2212, and playback of music is resumed.

In some embodiments block 2204 may be implemented by a hardware or software module which may be referred to as a "geographic location identification module", block 2208 may be implemented by a hardware of software module which may be referred to as an "intersection determining module", and blocks 2210 and/or 2212 may be implemented by a hardware or software module which may be referred to as a "playback module".

Figure 23:
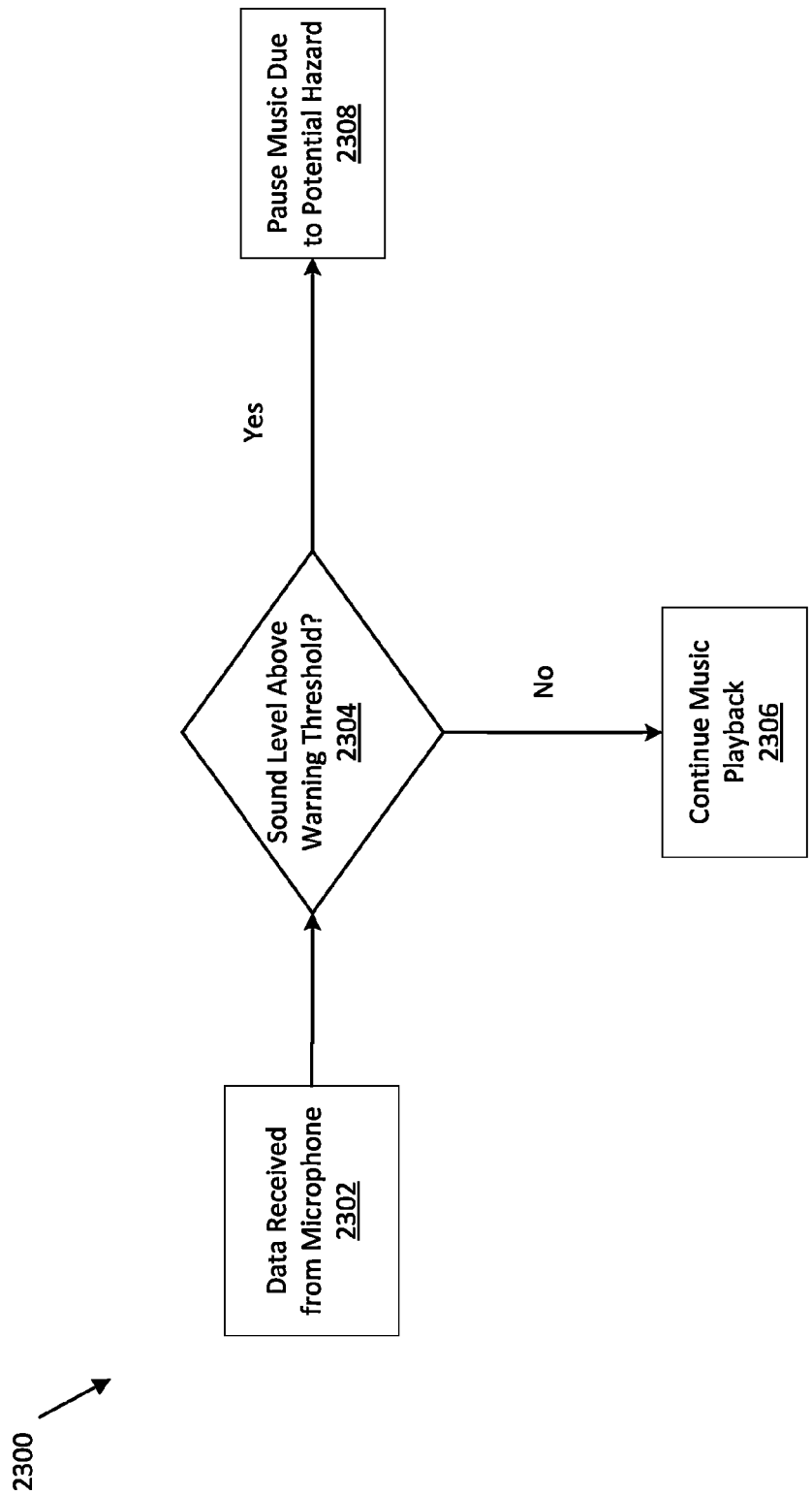
FIG. 23 illustrates one or more processes for pausing playback of media content to user based upon data received from a microphone sensor.

FIG. 23 is a flowchart diagram including one or more processes for automatically pausing playback of music based upon received microphone data. In one example, flowchart 2300 commences at block 2302 with the receipt of one or more data points from a microphone sensor on a user-worn device. In one specific example, a user may wear a mobile phone during a training session, wherein said mobile phone includes a microphone sensor. Those of ordinary skill in the art will recognize that other types of devices may include audible sensors, without departing from this disclosure.

Upon receipt of one or more data points from a microphone sensor, the user-worn device may execute one or more processes, by processor 202, for example, to compare the received sensor data to one or more sound thresholds. As such, block 2304 of flowchart 2300 may represent one or more processes to determine whether received sound information is above one or more threshold values. In one example, a threshold value may be a warning threshold, wherein a sound level above said warning threshold may represent a potential hazard to the user. In one specific example, the systems and methods described herein may be utilized for detection of a vehicle sounding a siren/horn as a warning, wherein said siren/horn may not be readily audible to the user due to ongoing music playback. As such, upon determination, at decision 2304, that received data from a microphone sensor is above one or more threshold values and/or fits a profile, flowchart 2300 may proceed to block 2308, wherein one or more processes may be executed to automatically pause playback of music. In this way, a user may be alerted to a potential hazard in their immediate surroundings, for example, if the user is running roadside, and the like. Furthermore, if, at block 2304, the received sensor data is below one or more threshold values, flowchart 2300 proceeds to block 2306, whereby of the music is allowed to continue. In such instances, however, the user may be provided an option to pause playback of media.

Figure 24:
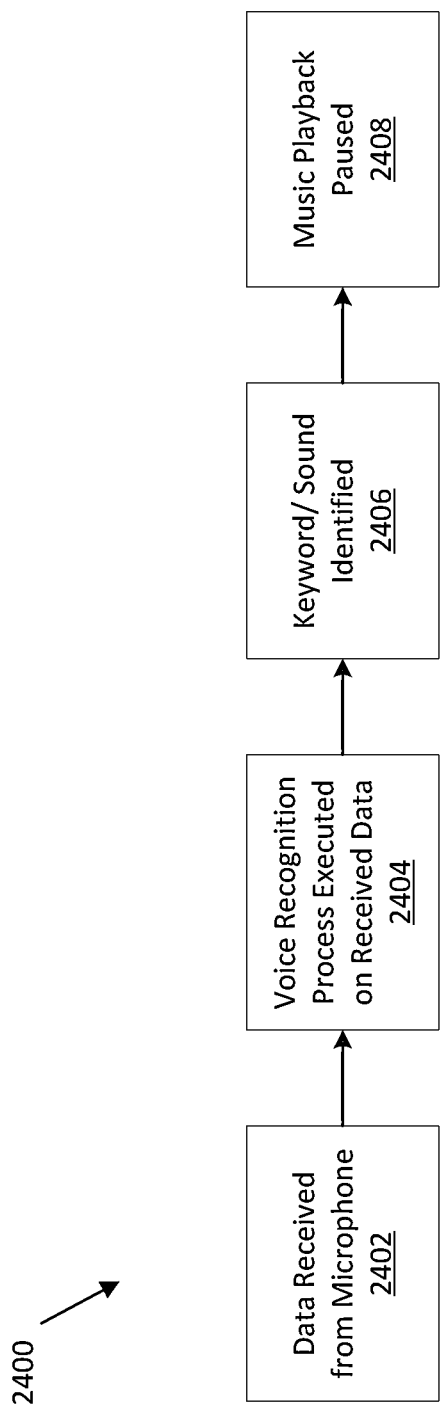
FIG. 24 depicts another flowchart including one or more processes for pausing playback of media content to user based upon data received from a microphone sensor.

FIG. 24 is a flowchart diagram representing one or more processes for automatically pausing playback of music based upon received microphone sensor data. In one example, flowchart 2400 commences at block 2402 with the receipt of one or more data points from a microphone sensor in a device worn by a user. In response to receipt of one or more data points from a microphone sensor, flowchart 2400 proceeds to block 2404, wherein block 2404 may represent one or more voice recognition processes. Accordingly, those of ordinary skill in the art will recognize various voice recognition processes that may be executed on received microphone sensor data at block 2404. Upon execution of one or more voice recognition processes, flowchart 2400 proceeds to block 2406, wherein block 3406 represents one or more processes to identify one or more keywords from the received voice data. In one example, a device which may be worn by a user may store, in memory, such as memory 212, one or more keywords or phrases, wherein a keyword or phrase may be, among others, "pause," "resume playback," among others. In this way, flowchart 2400 may represent one or more processes for pausing playback of music, and/or other media content, based upon spoken keywords/phrases. As such, upon identification of one or more keywords/phrases, flowchart 2400 proceeds to block 2408, wherein one or more processes are executed to pause playback of music, and the like. In one example, a keyword/phrase may be stored in memory, such as memory 212, in association with one or more attributes specific to a user, and such that a keyword/phrase spoken by a first user is identified at block 2406, but a same keyword/phrase spoken by a second user is not identified at block 2406, and the like.

Figure 25:
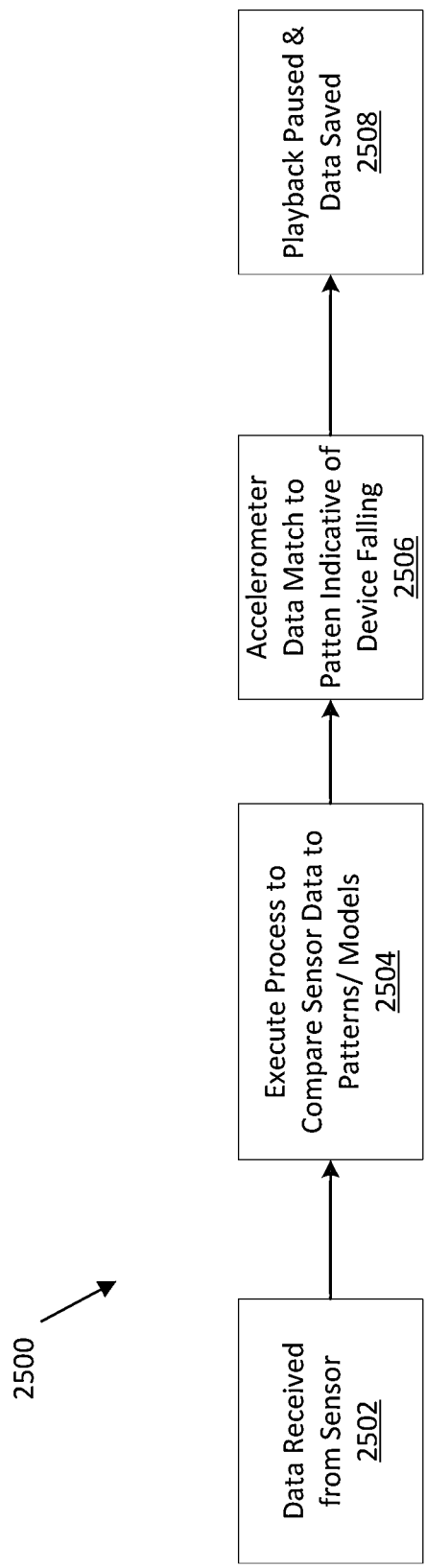
FIG. 25 is a flowchart illustrating one or more processes for pausing playback of media content based upon received accelerometer data.

FIG. 25 illustrates a flowchart diagram representing one or more processes for automatically pausing playback of media content based upon received data, such as from an accelerometer, indicative of a falling user device. In one example, block 2502 of flowchart 2500 represents one or more processes for receiving, by a device (which may be worn by a user during an athletic activity), accelerometer data from an accelerometer sensor. Block 2504 represents one or more processes for comparison of received accelerometer data to one or more acceleration patterns/models. In one example, the stored acceleration patterns/models are stored in a user device memory, such as memory 212, among others, and represent patterns of accelerometer data indicative of the user device being dropped/falling from a height. For example, one or more of the stored patterns/models may include a sudden increase/spike in acceleration data along one or more axes, and representative of the device falling to the ground.

Block 2506 of flowchart 2500 represents a determination that the received accelerometer data matches/is within a predetermined confidence interval of an accelerometer data pattern/model indicative of a user device being dropped. In this way, flowchart 2500 may be utilized to pause playback of playing music if it is determined that a user has dropped the mobile playback device, as indicated at block 2508. Additionally, detection of a drop may allow for one or more processes to be executed to save/backup data (locally and/or remotely, wherein remote backup may include uploading of data over a wireless network) from the device, and such that in the event of a catastrophic failure as a result of the drop, no athletic data, or equivalent, is lost.

Figure 26:
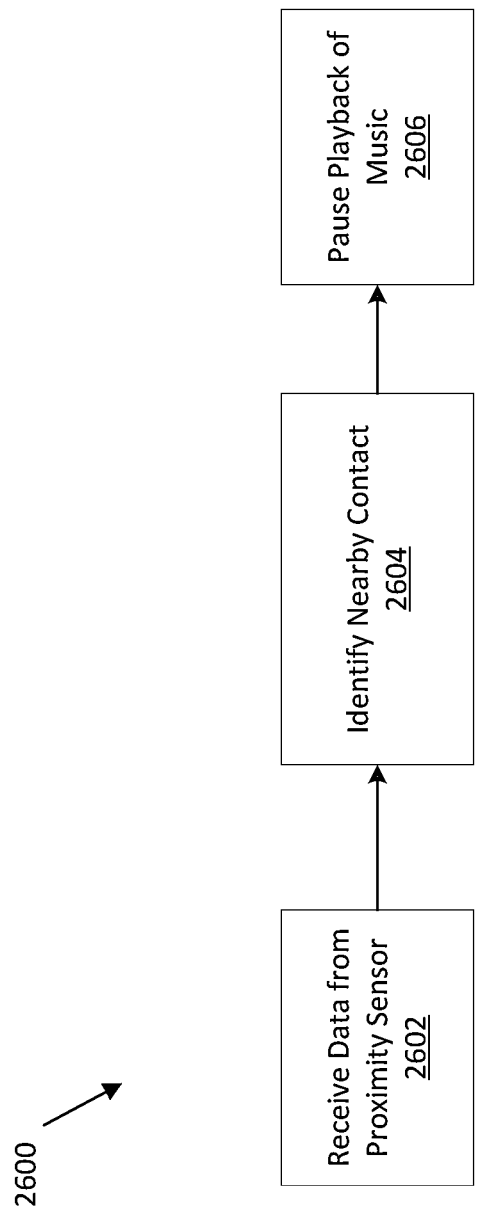
FIG. 26 illustrates one or more processes for pausing playback of media content based upon data received from a proximity sensor.

FIG. 26 is a flowchart diagram representing one or more processes for pausing playback of music based upon a proximity of a user to a known contact and/or location. In one example, and at block 2602, a processor, such as processor 202 of a device, such as device 112, 114, 126, 128, 130, 400 and/or 508, may receive one or more data points from a proximity sensor. In one example, a proximity sensor may be a NFC sensor, an RFID sensor, or may detect proximity based upon geographic location determined from a GPS sensor, or network information determined from a cellular and/or Internet network, among others. Accordingly, a proximity sensor may detect a beacon device within a predetermined distance of the proximity sensor, wherein a beacon device may be another device of the same type as that sensor present in the device, such as device 112, 114, 126, 128, 130, 400, and/or 508. In this way, in one example, an NFC sensor may be configured to transmit a signal indicating a user's presence, in addition to receiving signals from other NFC sensors. In another example, a beacon may be a QR code, or an electronic circuit configured to transmit information identifying a location and/or a user, among others. As such, a proximity sensor associated with a first user of a device may be utilized to detect a second user within a predetermined distance of the proximity sensor.

In one example, block 2602 may represent one or more processes for receiving sensor data from an NFC sensor. Accordingly, and at block 2604, one or more processes may be executed to identify a known contact and/or a known location from the received NFC data. In one specific example, a known contact may be identified as a result of a user positioning his/her worn device within a predetermined distance of a second device associated with a second user. In one example, this received data may be indicative of a friend of a user being within a predetermined distance of the user's location. As a result, and as indicated at block 2606, one or more processes may be executed to pause playback of music on the user's device.

Figure 27:
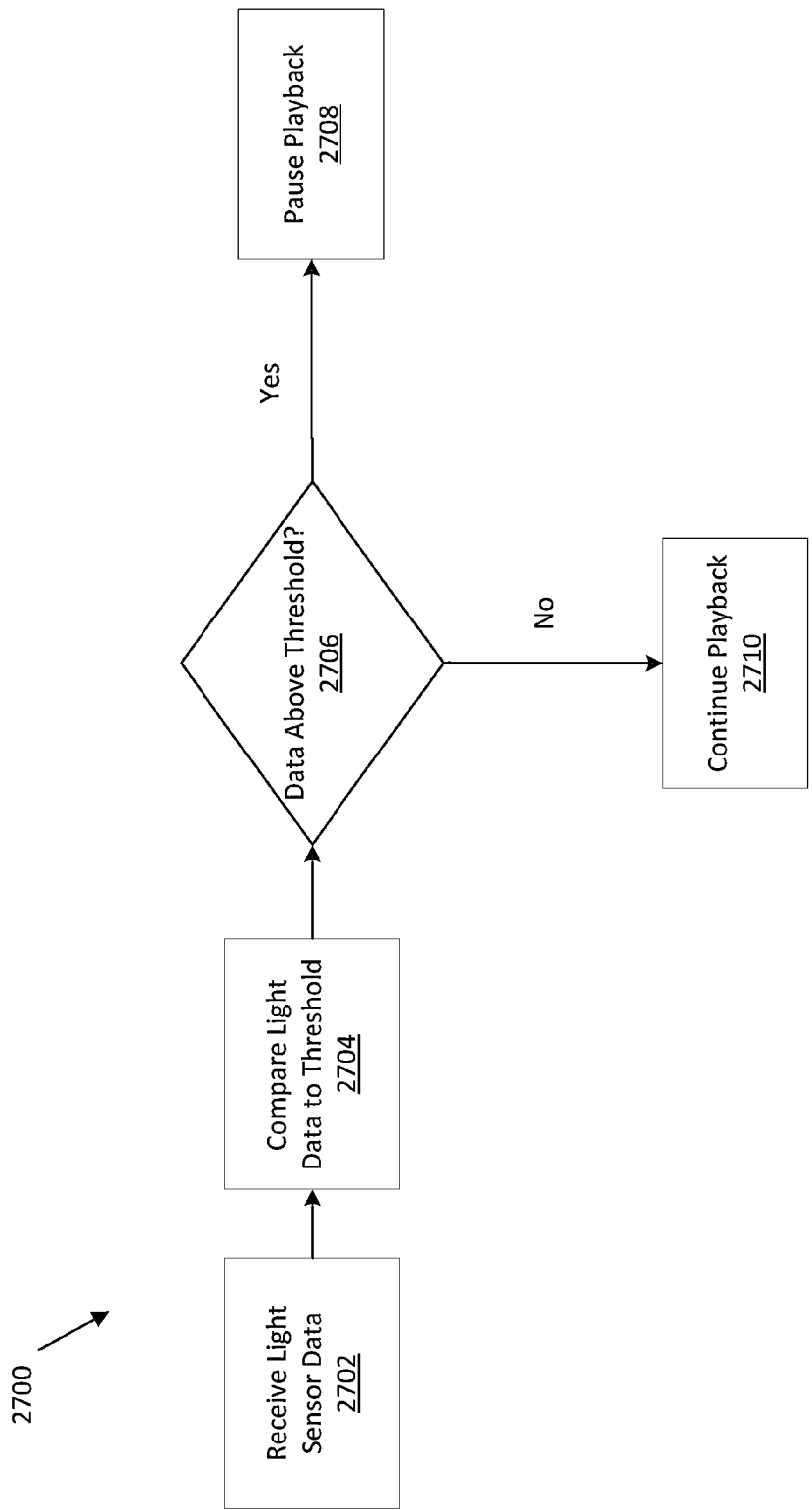
FIG. 27 illustrates one or more processes for pausing playback of media content based upon received light sensor data.

FIG. 27 is a flowchart diagram representing one or more processes to automatically pause playback of music on a user-worn device upon detection of a change in a light intensity by a light sensor of the device. Block 2702 of flowchart 2700 represents one or more processes for receiving light sensor data from a light sensor associated with a user-worn device. In one specific example, a mobile phone worn/carried by a user during an athletic activity, such as a running session, may include a light sensor. As such, and at block 2704, the received light sensor data may be compared to one or more light thresholds. If, at block 2706, it is determined that the received light sensor data is above one or more light thresholds, block 2708 executes one or more processes to pause playback of currently playing music from the device. Conversely, if a received light sensor data is below one or more thresholds, flowchart 2700 proceeds to block 2710, and playback of the music continues. As such, flowchart 2700 may be utilized to pause playback when, for example, a user extracts a device, such as a mobile telephone, from a pocket, and the like. In this example, the light sensor may detect a low level of ambient light when the mobile telephone is in a user's pocket, and wherein the intensity of light incident on the light sensor may be above one or more threshold values upon extraction of the mobile telephone from the user's pocket.

Figure 28:
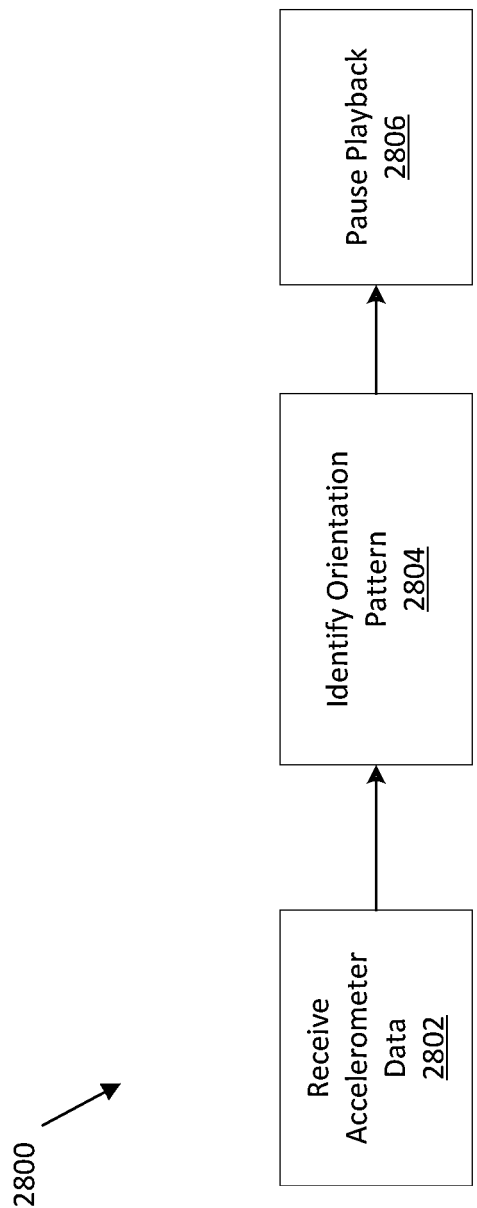
FIG. 28 illustrates one or more processes for pausing playback of media content of the user based upon received accelerometer data.

FIG. 28 is a flowchart diagram illustrating one or more processes for automatic pausing of playback based upon received accelerometer data. Similar to FIG. 20 and FIG. 25, block 2802 of flowchart 2800 may represent one or more processes to receive one or more data points from an accelerometer sensor associated with a user device, wherein said user device may be worn during an athletic activity, such as a running session. In one example, accelerometer data received from the accelerometer sensor may be representative of an orientation of the user device. For example, accelerometer data may be indicative of a user device "facing up," or "facing down," and the like. In another example, received accelerometer data at block 2802 may represent one or more changes in orientation of the user device, such as, for example, the user device transitioning from facing up to facing down and back, among others. Looking to block 2804, one or more processes may be executed to identify one or more patterns in the accelerometer data, wherein a pattern may be associated with one or more changes in orientation of the device. In one specific example, an orientation pattern may be associated with a transition from a device facing in an upward direction to facing in a downward direction, and wherein the device may be facing in an upward direction when held within a user's hand with a longitudinal axis of the device in a substantially horizontal orientation and having a screen of the device facing towards the sky. Correspondingly, the device may face in a downward direction when held in a user's hand with a longitudinal axis in a substantially horizontal orientation, and with the screen of the device facing towards the ground. As such, in this example, upon recognition of a transition from an upward direction to a downward direction, one or more processes may be executed, at block 2806, to pause playback of music.

It will be readily apparent to those of skill in the art that a captured first data value, such as, for example, at a first instance, and a captured second data value, such as, for example, at a second instance, may be during a same/continuous power cycle of a sensor, or an associated apparatus. As such, a sensor may capture a first and a second data value without powering down, or without switching into a low power mode, and the like. In another example, a sensor may capture a first and a second data point during a same athletic training session, wherein in one example, an athletic training session may include a sensor sampling data without entering into a lower power operational mode, and the like.

Embodiments of the invention may provide an apparatus which has enhanced safety features, for example. In certain embodiments, the apparatus may determine that a user is at a road intersection, junction, or the like, and may pause the playback of media such that the user can hear any traffic more clearly.

In certain embodiments, the automatic pausing of the playback of media may simplify the operation of the apparatus and may result in a more compact, power efficient, and less complex apparatus. The automatic pausing of the playback of media may provide ease-of-use benefits to the user, and may result in an apparatus that is safer to operate.

In any of the above aspects, the various features may be implemented in hardware, or as software modules running on one or more processors. Features of one aspect may be applied to any of the other aspects.

There may also be provided a computer program or a computer program product for carrying out any of the methods described herein, and a computer readable medium having stored thereon a program for carrying out any of the methods described herein. A computer program may be stored on a computer-readable medium, or it could, for example, be in the form of a signal such as a downloadable data signal provided from an Internet website, or it could be in any other form.

For the avoidance of doubt, the present application extends to the subject-matter described in the following numbered paragraphs (referred to as "Para" or "Paras"):"

1. A unitary apparatus configured to be worn by a user, comprising:
   a location-determining sensor arranged to capture location data of the user;
   a media content interface arranged to transmit information from media content to the user;
   a route storage module arranged to store a planned running route for the user;
   a geographic location identification module arranged to identifying, from data received by the location-determining sensor, a geographic location of the user;
   an intersection determining module arranged to utilize the identified geographic location of the user and the planned running route to identify an intersection within a predetermined distance ahead of the user on the planned running route; and
   a playback module arranged to pause playback of the media content until it is determined that the data captured by the location-determining sensor indicates that the user has crossed the intersection.

2. The unitary apparatus of Para 1, wherein the apparatus is configured to be worn on an appendage of the user.

3. The unitary apparatus of Para 1 or 2, wherein the apparatus comprises a mobile phone.

4. The unitary apparatus of any of Paras 1-3, wherein the media content interface comprises a headphone jack.

5. The unitary apparatus of any of Paras 1-4, wherein the predetermined distance is 15 meters.

6. The unitary apparatus of any of Paras 1-5, wherein the predetermined distance is 5 meters.

7. A unitary apparatus configured to be worn by a user, comprising:
   a sensor configured to capture motion data of the user;
   a media content interface;
   a training session module arranged to identify an athletic training session from the motion data, and arranged to identify a break in the athletic training session from the motion data; and
   a playback module arranged to pause playback of media content during the break in the athletic training session when a break in the athletic training session is identified.

8. The unitary apparatus of Para 7, wherein the training session module is arranged to identify a resumption of the athletic training session from the motion data, and wherein the playback module is arranged to resume playback of the media content upon when a resumption of the athletic training session is identified.

9. The unitary apparatus of Para 7 or 8, wherein the apparatus is configured to be worn on an appendage of the user.

10. The unitary apparatus of any of Paras 7-9, wherein the sensor comprises an accelerometer.

11. The unitary apparatus of any of Paras 7-10, wherein the sensor comprises a location-determining sensor.

12. The unitary apparatus of any of Paras 7-11, wherein the media content comprises a file selected from a group consisting of an audio file and a video file.

13. The unitary apparatus of any of Paras 7-12, wherein the media content interface comprises a headphone jack.

14. The unitary apparatus of any of Paras 7-13, wherein the media content interface comprises a display screen.

15. The unitary apparatus of any of Paras 7-14, wherein the media content interface comprises a wireless connection.

16. The unitary apparatus of any of Paras 7-15, wherein the athletic training session is a running session and wherein the break in the athletic training session corresponds to the user having stopped running 17. An apparatus, comprising:
   a processor;
   a sensor;
   a media content interface configured to transmit media content to a user; and
   memory storing computer-readable instructions that, when executed by the processor, cause the apparatus to:
      capture from the sensor, a first data value at a first instance and a second data value at a second instance, wherein the first instance is before the second instance; and
      determine that the first data value is equal to or above the threshold value, and in response, pausing a playback of media content to a user of the apparatus, and
      determining that the second data value is below the threshold value, the playback of the media content is resumed.

18. The apparatus of Para 17, wherein the sensor comprises at least one light sensor and wherein the threshold value is a light intensity value.

19. The apparatus of Para 17 or 18, wherein the sensor is a proximity sensor, and wherein the threshold value is referenced to a distance that the user is away from a beacon device.

20. The apparatus of Para 19, wherein the first and the second instances are during a single power cycle of the apparatus.

21. The apparatus of any of Paras 17-20, wherein the apparatus is a unitary apparatus configured to be worn by a user.

22. A unitary apparatus according to any of Paras 1-17 or 21, wherein the unitary apparatus is configured to be worn around an appendage, such as a wrist, of a user.

23. A non-transitory computer-readable medium comprising executable instructions that when executed cause a computer device to function as a unitary apparatus or apparatus as described in any of Paras 1-22.

24. A method of controlling the playback of media content to a user from a unitary apparatus configured to be worn by a user, comprising:
  capturing location data of the user;
  identifying from the location data a geographic location of the user; and
  utilizing the identified geographic location of the user and a planned running route to identify an intersection within a predetermined distance ahead of the user on the planned running route; and
  pausing playback of the media content until it is determined that the location data indicates that the user has crossed the intersection.

25. A method of controlling the playback of media content to a user from a unitary apparatus configured to be worn by a user, comprising:
  capturing motion data of the user;
  identifying an athletic training session from the motion data,
  identifying a break in the athletic training session from the motion data; and
  when a break in the athletic training session is identified, pausing playback of the media content during the break in the athletic training session.

26. A method of controlling the playback of media content to a user, comprising:
  capturing from a sensor a first data value at a first instance and a second data value at a second instance, wherein the first instance is before the second instance; and
  determining that the first data value is equal to or above the threshold value, and in response, pausing playback of the media content, and
  determining that the second data value is below the threshold value, and in response, resuming playback of the media content.

27. A non-transitory computer-readable medium comprising executable instructions that when executed cause a computer device to perform the method as described in any of Paras 24-26.

28. An apparatus, such as a unitary apparatus arranged to be won by a user, comprising the computer-readable medium of Para 27.

29. A unitary apparatus configured to be worn by a user, comprising:
  a processor;
  a location-determining sensor configured to capture location data of the user;
  a media content interface configured to transmit information from media content to the user; and
  a non-transitory computer-readable medium storing a planned running route for the user, wherein the computer-readable medium further comprises computer-executable instructions that when executed by the processor perform at least:
  identifying, from data received by the location-determining sensor, a geographic location of the user;
  utilizing the identified geographic location of the user and the planned running route to identify an intersection within a predetermined distance ahead of the user on the planned running route; and
  pausing playback of the media content until data received by the location-determining sensor indicates that the user has crossed the intersection.

30. The unitary apparatus of para 29, wherein the apparatus is configured to be worn on an appendage of the user.

31. The unitary apparatus of para 29, wherein the apparatus comprises a mobile phone.

32. The unitary apparatus of para 29, wherein the media content interface is a headphone jack.

33. The unitary apparatus of para 29, wherein the predetermined distance is 15 meters.

34. The unitary apparatus of para 29, wherein the predetermined distance is 5 meters.

35. A unitary apparatus configured to be worn by a user, comprising:
  a processor;
  a sensor configured to capture motion data of the user;
  a media content interface; and
  a non-transitory computer-readable medium comprising computer-executable instructions that when executed by the processor perform at least:
  capturing, from the sensor while being worn on the user, motion data generated by the sensor as a result of a motion of the user;
  identify an athletic training session from the motion data;
  identify a break in the athletic training session from the motion data; and
  pause playback of media content during the break in the athletic training session.

36. The unitary apparatus of para 35, wherein the computer-readable medium of the unitary apparatus comprises further instructions that when executed by the processor, perform at least:
  resume playback of the media content upon identification of a resumption in the athletic training session, wherein the identification is based upon the motion data.

37. The unitary apparatus of para 35, wherein the apparatus is configured to be worn on an appendage of the user.

38. The unitary apparatus of para 35, wherein the sensor comprises an accelerometer.

39. The unitary apparatus of para 35, wherein the sensor comprises a location-determining sensor.

40. The unitary apparatus of para 35, wherein the media content comprises a file selected from a group consisting of an audio file and a video file.

41. The unitary apparatus of para 35, wherein the media content interface is a headphone jack.

42. The unitary apparatus of para 35, wherein the media content interface comprises a display screen.

43. The unitary apparatus of para 35, wherein the media content interface comprises a wireless connection.

44. The unitary apparatus of para 35, wherein the athletic training session is a running session and the break in the athletic training session corresponds to the user having stopped running 45. An apparatus, comprising:
  a processor;
  a sensor;
  a media content interface configured to transmit media content to a user; and
  memory storing computer-readable instructions that, when executed by the processor, cause the apparatus to:
  capture from the sensor, a first data value at a first instance and a second data value at a second instance, wherein the first instance is before the second instance; and determine that the first data value is equal to or above the threshold value, and in response, pausing a playback of media content to a user of the apparatus, and determining that the second data value is below the threshold value, the playback of the media content is resumed.

46. The apparatus of para 45, wherein the sensor comprises at least one of a light sensor and the threshold value is a light intensity value.

47. The apparatus of para 45, wherein the sensor is a proximity sensor, and wherein the threshold value is referenced to a distance that the user is away from a beacon device.

48. The apparatus of para 47, wherein the first and the second instances are during a single power cycle of the apparatus.

What is claimed is:

1. A unitary apparatus configured to be worn by a user, comprising:
   a processor;
   a location-determining sensor configured to capture location data of the user;
   a media content interface configured to transmit information from media content to the user; and
   a non-transitory computer-readable medium having computer-executable instructions that when executed by the processor comprise a planned running route for the user, wherein the computer-readable medium further comprises computer-executable instructions that when executed by the processor perform at least:
      identifying, from data received by the location-determining sensor, a geographic location of the user;
      utilizing the identified geographic location of the user and the planned running route to identify an intersection within a predetermined distance ahead of the user on the planned running route; and
      pausing playback of the media content based upon the user being within the predetermined distance, wherein the media content remains paused at least until data received by the location-determining sensor indicates that the user has crossed the intersection.

2. The unitary apparatus of claim 1, wherein the predetermined distance is a first predetermined distance, and wherein the non-transitory computer-readable medium further comprises computer-executable instructions that when executed by the processor perform at least:
   after pausing playback of the media content, determining the geographic location of the user to determine if the user is within a second predetermined distance from the intersection; and
   upon determining that the user is not within the second predetermined distance, resuming playback of the media content.

3. The unitary apparatus of claim 2, wherein the first predetermined distance is equal to the second predetermined distance.

4. The unitary apparatus of claim 1, wherein the apparatus is configured to be worn on an appendage of the user.

5. The unitary apparatus of claim 1, wherein the apparatus comprises a mobile phone.

6. The unitary apparatus of claim 1, wherein the media content interface comprises at least one of a headphone jack, a display screen, and a wireless connection.

7. The unitary apparatus of claim 1, wherein the predetermined distance is either 15 meters or 5 meters.

* * * * *